(12) United States Patent
Chiu et al.

(10) Patent No.: US 11,925,650 B2
(45) Date of Patent: Mar. 12, 2024

(54) ANTIBACTERIAL CHEMICAL COMPOUND, ITS MANUFACTURING METHOD AND ITS USE THEREOF

(71) Applicants: National Taiwan University, Taipei (TW); National Yang Ming Chiao Tung University, Taipei (TW)

(72) Inventors: Hao-Chieh Chiu, Taipei (TW); Chung-Wai Shiau, Taipei (TW)

(73) Assignees: NATIONAL TAIWAN UNIVERSITY, Taipei (TW); NATIONAL YANG MING CHIAO TUNG UNIVERSITY, Taipei (TW)

( * ) Notice: Subject to any disclaimer, the term of this patent is extended or adjusted under 35 U.S.C. 154(b) by 0 days.

(21) Appl. No.: 17/686,949

(22) Filed: Mar. 4, 2022

(65) Prior Publication Data
US 2023/0277551 A1 Sep. 7, 2023

(51) Int. Cl.
| | |
|---|---|
| *A61K 31/5513* | (2006.01) |
| *A61K 31/165* | (2006.01) |
| *A61K 31/431* | (2006.01) |
| *A61K 31/496* | (2006.01) |
| *A61K 31/5383* | (2006.01) |
| *A61K 31/65* | (2006.01) |
| *A61K 31/7036* | (2006.01) |
| *A61P 31/04* | (2006.01) |
| *C07D 495/04* | (2006.01) |

(52) U.S. Cl.
CPC ........ *A61K 31/5513* (2013.01); *A61K 31/165* (2013.01); *A61K 31/431* (2013.01); *A61K 31/496* (2013.01); *A61K 31/5383* (2013.01); *A61K 31/65* (2013.01); *A61K 31/7036* (2013.01); *A61P 31/04* (2018.01); *C07D 495/04* (2013.01)

(58) Field of Classification Search
None
See application file for complete search history.

(56) References Cited

U.S. PATENT DOCUMENTS

2019/0125825 A1* 5/2019 Blackledge ............. A61P 31/04

FOREIGN PATENT DOCUMENTS

WO WO-2009137499 A1 * 11/2009 ........... C07D 243/38

OTHER PUBLICATIONS

Cheng-Yun Hsu et al., "A Novel Dibenzoxazepine Attenuates Intracellular *Salmonella typhimurium* Oxidative Stress Resistance", Dec. 1, 2021, 10 pages, Microbiology Spectrum, vol. 9, Issue 3.

* cited by examiner

*Primary Examiner* — Zinna Northington Davis
(74) *Attorney, Agent, or Firm* — MUNCY, GEISSLER, OLDS & LOWE, P.C.

(57) ABSTRACT

The present invention provides an antibacterial chemical compound, its manufacturing method and its use thereof which acts as antibacterial agents being useful for treating a disease or condition characterized by infectious disease, such as gastroenteritis and invasive non-typhoidal Salmonellosis, and also providing a new therapeutic option for patients infected by the bacteria with the resistance to antibiotics.

13 Claims, 7 Drawing Sheets

ANTIBACTERIAL CHEMICAL COMPOUND, ITS MANUFACTURING METHOD AND ITS USE THEREOF

BACKGROUND OF THE INVENTION

1. Technical Field

The present invention relates to an antibacterial chemical compound, its manufacturing method and its use thereof.

2. Description of Related Art

Bacterial infection is a common disease with high morbidity and high mortality that endangers humans. The emergence of multidrug resistance has further dampened the treatment and increased the mortality of infected persons.

During infection, bacteria can express a variety of virulence factors to invade the host cells and evade the attacks of host defense mechanisms. For example, macrophages can exploit multi-subunit NADPH-dependent phagocytic oxidase (Phox or NOX2) to generate reactive oxygen species (ROS) as a key defense mechanism against invading bacteria. NOX2 assembles on the phagolysosomal membrane, reducing oxygen to produce superoxide anions, which are then enzymatically or spontaneously reduced to different kinds of ROS, including hydrogen peroxide and hydroxyl radicals. All of these ROS can control invasive microorganisms, but the detailed mechanisms have not been completely clarified. In contrast, bacteria are capable of secreting antioxidants via efflux pumps. Thus, blocking the efflux pump channel by the small molecules is a potential strategy to control bacterial infections

BRIEF SUMMARY OF THE INVENTION

In view of the aforementioned reasons, after developing a cell-based assay and identifying several compounds that can inhibit intracellular bacteria via a virulence-targeted mechanism, the inventors of the present application found compounds having special chemical structures, which can attenuate bacterial resistance to oxidative stress and is beneficial to patients with bacterial infections. Thus the inventors completed the present invention of antibacterial chemical compound, its manufacturing method and its use thereof.

An aspect of the present invention provides a compound (I) having following structure:

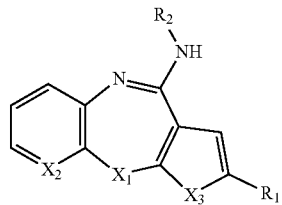

(I)

or a pharmaceutically acceptable salt thereof, wherein
$X_1$ is NH or O;
$X_2$ is N or CH;
$X_3$ is S or CHCH;
$R_1$ is H, $CH_3$ or Cl; and $R_2$ is an alkyl or an alkyl amine or alkyl aromatic ring group.

In one or more embodiments of the compound (I), wherein $R_2$ is:

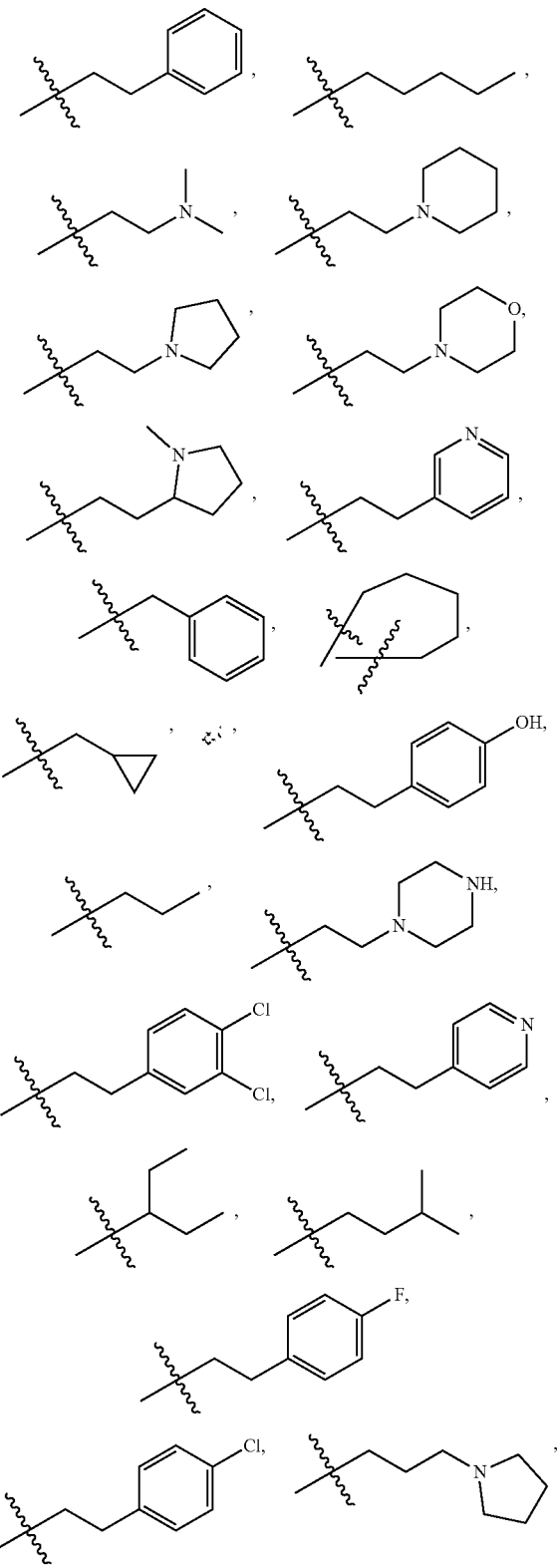

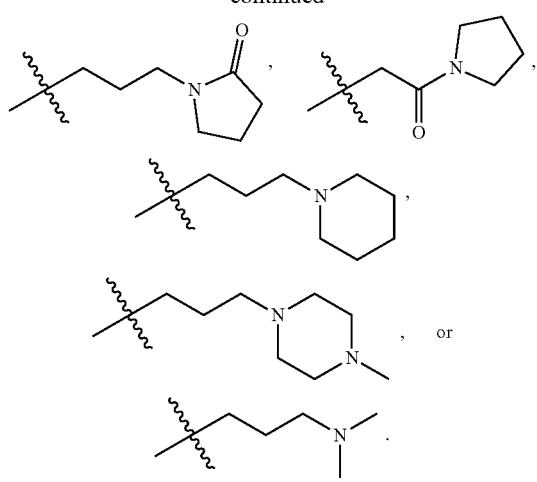

An another aspect of the present invention is to provides a pharmaceutical composition comprising: an effective amount of a compound (I) having following structure:

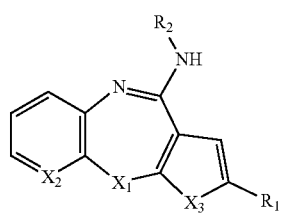
(I)

or a pharmaceutically acceptable salt thereof,
wherein
$X_1$ is NH or O;
$X_2$ is N or CH;
$X_3$ is S or CHCH;
$R_1$ is H, $CH_3$ or Cl; and
$R_2$ is an alkyl or an alkyl amine or alkyl aromatic ring group.

In one or more embodiments of the pharmaceutical composition, wherein $R_2$ is:

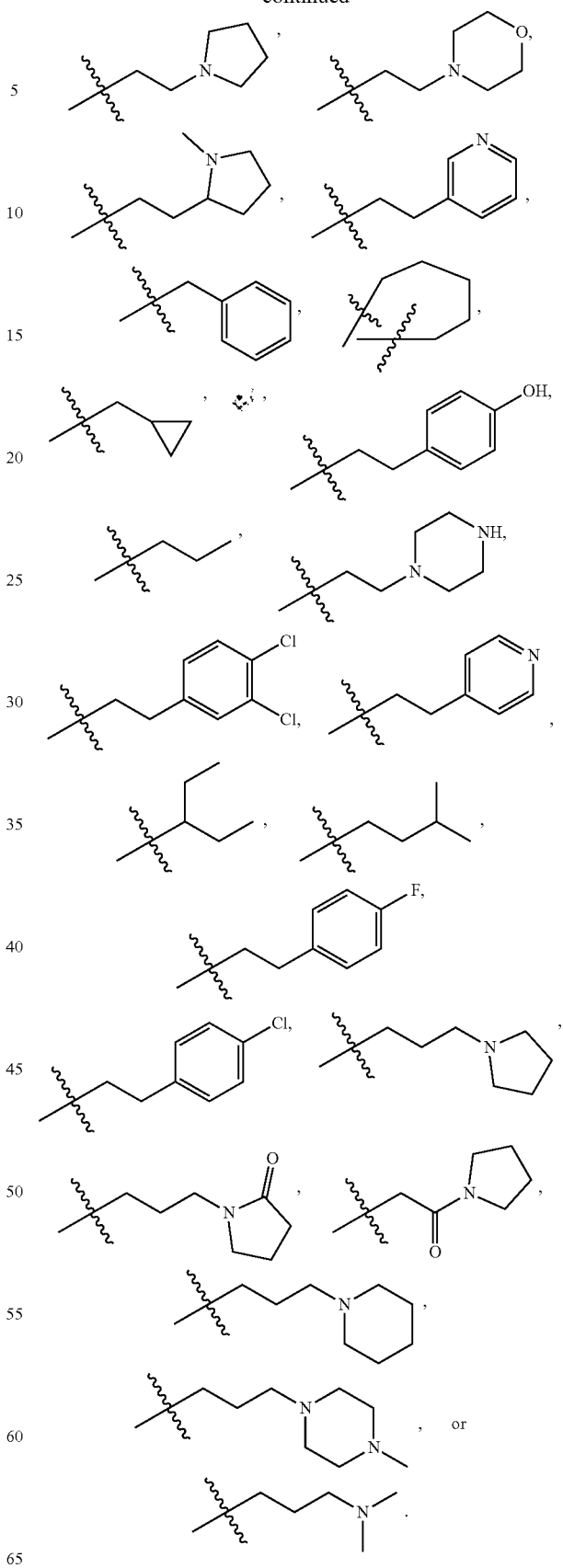

In one or more embodiments of the pharmaceutical composition, wherein the compound is:

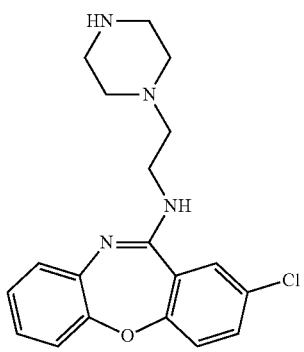 [SMILES: Clc1ccc2c(c1)C(NCCN1CCNCC1)=Nc1ccccc1O2]

In one or more embodiments, the pharmaceutical composition further comprises a pharmaceutically acceptable excipient.

In one or more embodiments, the pharmaceutical composition further comprises an antibiotic.

In one or more embodiments, the pharmaceutical composition targets a bacteria's resistance to host oxidative-stress defense.

In one or more embodiments, the pharmaceutical composition targets to multidrug-resistant strain bacteria.

In one or more embodiments, the bacteria is selected from the group consisting of: *Staphylococcus aureus*, *Staphylococcus haemolyticus*, *Staphylococcus hominis*, *Staphylococcus intermedius*, *Staphylococcus saprophyticus*, *Staphylococcus lugdunesis*, *Erysipelothrix rhusiopathiae*, *Enterococcus faecalis*, *Enterococcus faecium*, VR-*E. faecium*, *Bacillus cereus*, *Bacillus subtilis*, *Corynebacterium diphtheriae*, *Listeria monocytogenes*, *Streptococcus pyogenes*, *Clostridium difficile*, *Escherichia coli*, *Salmonella Typhimurium*, *Acinetobacter baumannii*, and *Mycobacterium tuberculosis*.

An another aspect of the present invention is to provide a method of synthesizing the compound (I), comprising:
(1) reacting a compound (VI) of the following structure

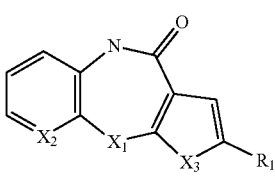

(VI)

with $POCl_3$ and $R_2NH_2$ to obtain the compound (I); or
(2) reacting a compound (XVI) of the following structure

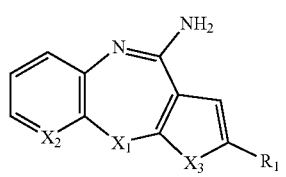

(XVI)

with $R_2NH_2$ to obtain the compound (I);
wherein $X_1$, $X_2$, $X_3$, $R_1$ and $R_2$ are the same as defined above.

In one or more embodiments of the method of synthesizing the compound (I), wherein $X_1$ of the compound (VI) is O and the compound (VI) is obtained by
(a) under the present of $K_2CO_3$, reacting a compound (II) of following structure

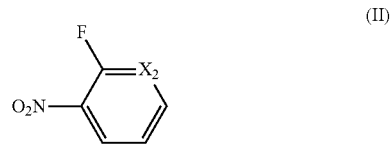

(II)

with a compound (III) of following structure

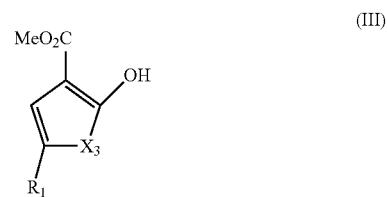

(III)

to obtain a compound (IV) of following structure;

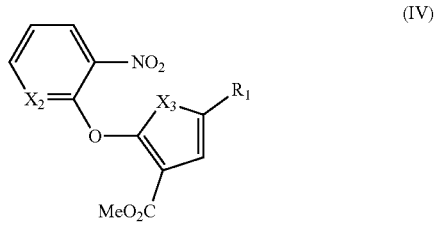

(IV)

(b) reacting the compound (IV) with $SnCl_2$ to obtain a compound (V) of following structure;

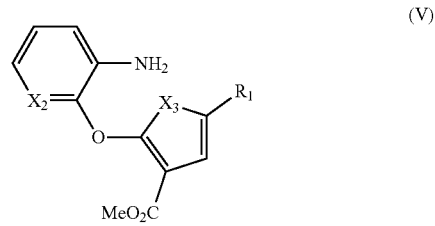

(V)

(c) reacting the compound (V) with $H_2SO_4$ to obtain the compound (VI);
wherein $X_2$, $X_3$, $R_1$ and $R_2$ are the same as defined above.

In one or more embodiments of the method of synthesizing the compound (I), wherein $X_1$ of the compound (VI) is NH and the compound (VI) is obtained by:
(a) under the present of $SOCl_2$, reacting a compound (VII) of following structure

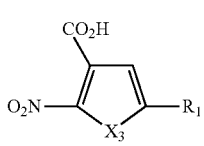           (VII)

with a compound (VIII) of following structure

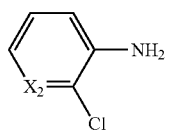           (VIII)

to obtain a compound (IX) of following structure;

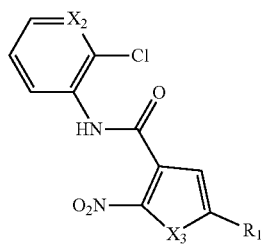           (IX)

(b) reacting the compound (IX) with SnCl$_2$ to obtain a compound (X) of following structure;

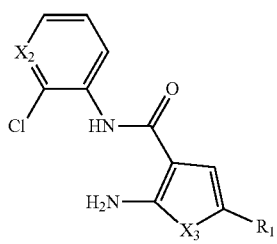           (X)

(c) reacting the compound (X) with DEGMME to obtain the compound (VI);
wherein X$_2$, X$_3$, R$_1$ and R$_2$ are the same as defined above.

In one or more embodiments of the method of synthesizing the compound (I), wherein X$_1$ is NH and the compound (VI) is obtained by:
(a) reacting a compound (XI) of following structure

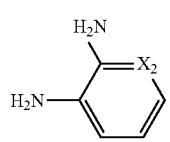           (XI)

with a compound (XII) of following structure with Cu and K$_2$CO$_3$

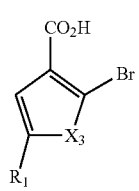           (XII)

to obtain a compound (XIII) of following structure;

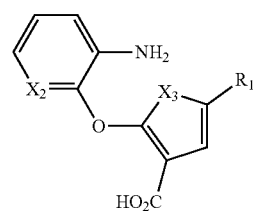           (XIII)

(b) reacting the compound (XIII) with H$_2$SO$_4$ to obtain the compound (VI);
wherein X$_2$, X$_3$, R$_1$ and R$_2$ are the same as defined in claim 1.

In one or more embodiments of the method of synthesizing the compound (I),
wherein X$_1$ is NH and the compound (XVI) is obtained by:
(a) reacting a compound (II) of following structure

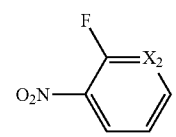           (II)

with a compound (XIV) of following structure

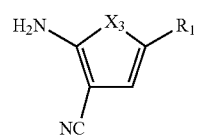           (XIV)

to obtain a compound (XV) of following structure;

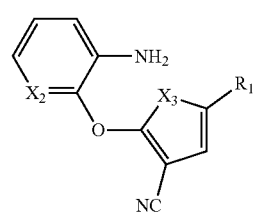          (XV)

(b) reacting the compound (XV) with SnCl$_2$ and HCl to obtain the compound (XVI);
wherein X$_2$, X$_3$, R$_1$ and R$_2$ are the same as defined above.

Thereby, the compound of the present invention can act as antibacterial agents being useful for treating a disease or condition characterized by infectious disease, such as gastroenteritis and invasive non-typhoidal Salmonellosis, and also provides a new therapeutic option for patients infected by the bacteria with the resistance to antibiotics.

DETAILED DESCRIPTION OF THE INVENTION

Figure 1:
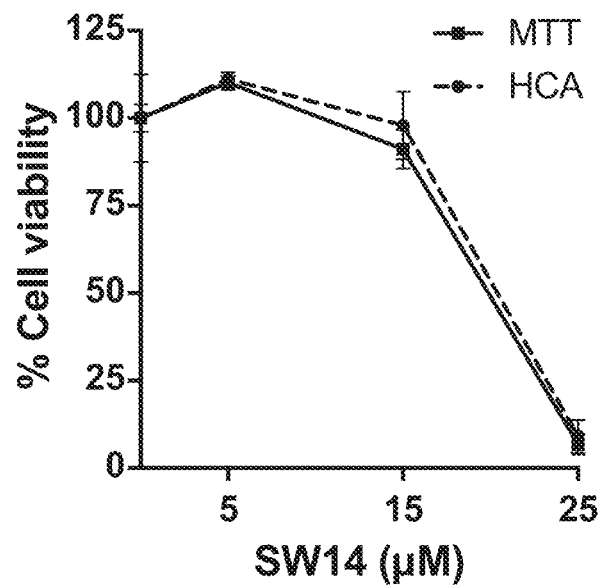
FIG. 1. Cell viability of RAW264.7 cells treated with 0, 5, 15, and 25 μM of SW14. The cell viability was evaluated using HCA and an MTT cell viability assay, and the data are expressed as a percentage relative to the untreated control and are presented as the mean±SD (n=3 per group).

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

As used herein, the terms "comprising," "having," and "including" are used in their open, non-limiting sense. The terms "a," "an," and "the" are understood to encompass the plural as well as the singular. The expression "one or more" means "at least one" and thus may include an individual characteristic or mixtures/combinations.

The invention provides a compound (I) having following structure:

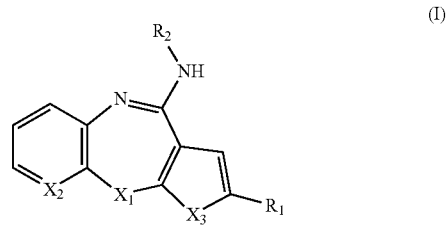

or a pharmaceutically acceptable salt thereof, wherein $X_1$ is NH or O; $X_2$ is N or CH; $X_3$ is S or CHCH; $R_1$ is H, $CH_3$ or Cl; and $R_2$ is an alkyl or an alkyl amine or alkyl aromatic ring group.

The invention also provides a pharmaceutical composition comprising: an effective amount of a compound (I) having following structure:

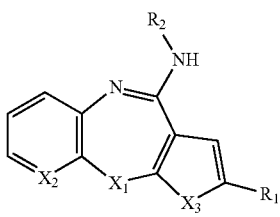

(I)

or a pharmaceutically acceptable salt thereof, wherein $X_1$ is NH or O; $X_2$ is N or CH; $X_3$ is S or CHCH; $R_1$ is H, $CH_3$ or Cl; and $R_2$ is an alkyl or an alkyl amine or alkyl aromatic ring group.

The invention also provides a method of synthesizing the compound (I), comprising:
(1) reacting a compound (VI) of the following structure

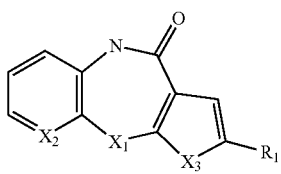

(VI)

with $POCl_3$ and $R_2NH_2$ to obtain the compound (I); or
(2) reacting a compound (XVI) of the following structure

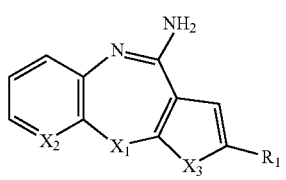

(XVI)

with $R_2NH_2$ to obtain the compound (I);
wherein $X_1$, $X_2$, $X_3$, $R_1$ and $R_2$ are the same as defined in claim 1.

As the term "pharmaceutically acceptable salt" used herein refers to pharmaceutically acceptable organic or inorganic salts of a compound of the invention. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate mesylate, ethanesulfonate, benzenesulfonate, p-toluenesulfonate, and pamoate (i.e., 1,1-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The desired pharmaceutically acceptable salt may be prepared by any suitable method available in the art. For example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

As the term "pharmaceutically acceptable" used herein refers that the substance or composition must be compatible chemically and/or toxicologically, with the other ingredients comprising a formulation, and/or the mammal being treated therewith.

As the term "pharmaceutical composition" used herein refers to a compound of the invention, or a pharmaceutically acceptable salt thereof, together with at least one pharmaceutically acceptable carrier. In certain embodiments, the pharmaceutical composition according to the invention is provided in a form suitable for topical, parenteral or injectable administration.

As the term "excipient" used herein refer to binders, filters, lubricants, wetting agents/surfactants, glidants, flavouring agents, sweetening agents, and other conventionally used in drug manufacture excipients.

Binders such as acacia mucilage, alginic acid, polyvinylpyrrolidone (povidone), gelatin, sucrose, starch mucilage, pregelatinised starch, starch paste, sodium alginate, sorbitol, tragacanth, glucose, hydroxypropylmethyl cellulose (HPMC), magnesium aluminium silicate, starch paste, polyvinylpyrrolidone, carboxymethylcellulose sodium, dextrin, ethyl cellulose, polyethylene glycol, guar gum, zein, hydroxyethyl cellulose, hydroxypropyl cellulose, methyl cellulose, polymethacrylates, and carboxymethylcellulose calcium;

Filters such as such as water-soluble fillers, like soluble lactose, compressible sugar, confectioners sugar, dextrose, mannitol, sodium chloride, sorbitol, xylitol, sodium chloride F, and water-insoluble fillers, like calcium carbonate, magnesium carbonate, calcium phosphate (e.g. di and tri basic calcium phosphate), calcium sulphate, kaolin, microcrystalline cellulose, powdered cellulose, pregelatinized starch, starch, barium sulphate, magnesium trisilicate, and aluminium hydroxide.

Lubricants such as stearates (e.g. magnesium or calcium stearate), talc, polyethylene glycol, liquid paraffin, sodium lauryl sulphate, magnesium lauryl sulphate, colloidal silicon dioxide, palmitostearate, stearic acid, zinc stearate, and hydrogenated vegetable oil.

Wetting agents/Surfactants such as sodium dodecyl sulphate, sodium lauryl sulphate, polyoxyethylene sorbitan fatty acid esters (Tweens), polyoxyethylene stearates, and sorbitan fatty acid esters (Spans).

Glidants such as talc, starch, magnesium stearate, and silica derivatives, like colloidal silica (e.g. Aerosil), pyrogenic silica, hydrated sodium silicoaluminate, and colloidal silicon dioxide.

Flavouring agents such as orange, cherry, strawberry, raspberry, grape, and passion fruit.

Sweetening agents such as sodium saccharin, aspartame, confectioners sugar, sorbitol, sucrose, and xylitol.

As the term "antibiotic" used herein refer to substances used to treat and/or prevent bacterial infections by killing bacteria, inhibiting bacterial growth or reducing bacterial viability. The antibiotic can be the first-line antibiotic such as amoxicillin, trimethoprim-sulfamethoxazole, and erythromycin; or the second-line antibiotic such as azithromycin, cefixime, ciprofloxacin, loracarbef, levofloxacin, metronidazole.

EXAMPLES

Synthesis of the Compound Having a Chemical Structure (I)

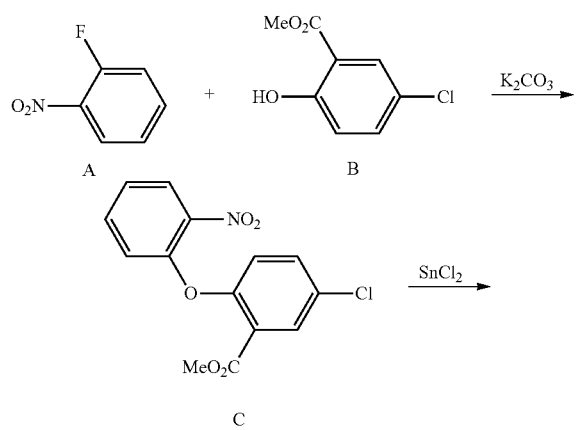

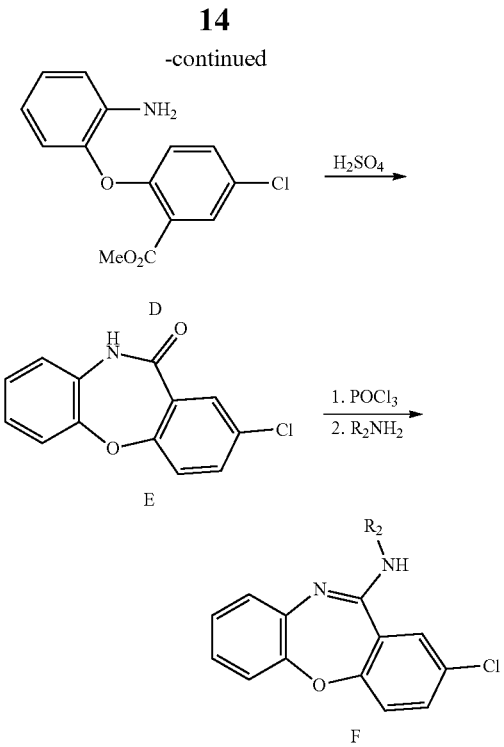

In the first step of synthesis scheme I, compound A was coupled with compound B to generate compound C in the present of $K_2CO_3$. In this step, $K_2CO_3$ was first added to a 1, 4-dioxane solution of the compound B. Next, compound A was added to the reaction mixture. The obtained reaction mixture was then stirred and heated to reflux temperature for 16 hours. After the reaction mixture was cooled to room temperature, NaOH solution was added thereto to quench the reaction. The reaction mixture was extracted with toluene. The collected organic phases were dried over anhydrous $MgSO_4$ and finally filtered. The filtrate was concentrated to obtain compound C.

In step 2, the compound C was reacted with $SnCl_2$ to obtain the compound D. In this step, a dried EtOH solution of the compound C was slowly added to a $SnCl_2$ solution. The mixture was stirred for 16 hours under a nitrogen atmosphere and concentrated under reduced pressure. The relation mixture was filtered through celite and washed with EtOAc. The filtrate was concentrated for chromatography. After purified with chromatography, compound D was obtained.

In step 3, the compound D was dissolved in DMF and the concentrated $H_2SO_4$ was added to the solution and refluxed for 16 hours under nitrogen atmosphere. The reaction mixture was cooled and poured in cold water. The precipitate was collected by filtration, washed with cold water, and dried under vacuum to obtain compound E.

In step 4, the compound E and $POCl_3$ were mixed in the flash at room temperature. After 10 minutes, dimethylacetamide was added dropwise and then refluxed for 16 hours. The excess $POCl_3$ was distilled out under reduced pressure and the residue was extracted with toluene and water. The toluene extract was dried over with anhydrous magnesium sulfate and concentrated under reduced pressure to generate crude compound. The crude compound (was dissolved in xylene and stirred at room temperature under nitrogen atmosphere. After 10 minutes, $R_2NH_2$ was added and then refluxed for 16 hours. The reaction mixture was poured into water. The resulting solution was alkalization by the addition of 2N aqueous solution of NaOH, and then extracted with EtOAc and water. The EtOAc extract was dried over with anhydrous magnesium sulfate and concentrated under reduced pressure. The crude product was purified by column chromatography on silica gel or aluminum oxide to obtain compound F.

In the synthesis scheme I, $R_2$ is an alkyl or an alkyl amine or alkyl aromatic ring group. The structure is defined as above.

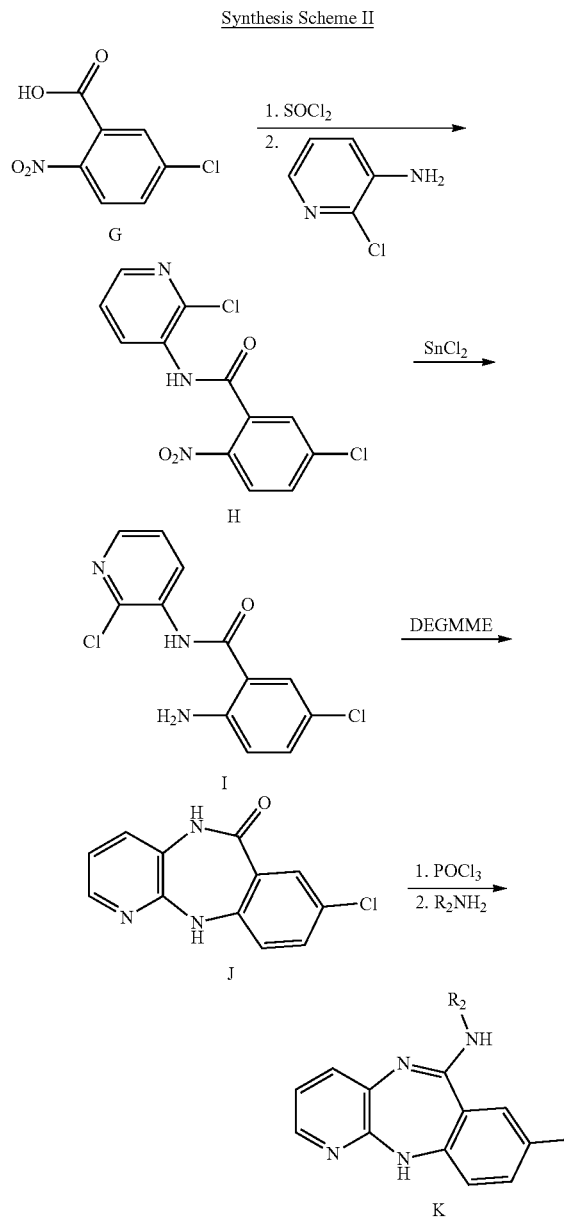

In the first step of synthesis scheme II, compound G was converted to intermediate acyl chloride in the present of $SOCl_2$. Next, the intermediate was added to the reaction mixture with 3-amino-2-chloropyridine. The obtained reaction mixture was then stirred and heated to reflux temperature for 16 hours. After the reaction mixture was cooled to room temperature, NaOH solution was added thereto to quench the reaction. The reaction mixture was extracted with EtOAc. The collected organic phases were dried over anhydrous $MgSO_4$ and finally filtered. The filtrate was concentrated to obtain compound H.

In step 2, the compound H was reacted with $SnCl_2$ to obtain the compound I. In this step, a dried EtOH solution of the compound I was slowly added to a $SnCl_2$ solution. The mixture was heated to 100° C. for 30 min, cooled, filtered and washed with water. The filtrate was basifying with 2N aqueous solution of and extracted with DCM and water. The DCM extract was dried over with anhydrous magnesium sulfate and concentrated at room temperature under reduced pressure to obtain compound I.

In step 3, the compound I in DEGMME was stirred for 16 hours at 150° C. under nitrogen atmosphere. The mixture and then cooled on ice, and the precipitate were collected by filtration, washed with MeOH, and dried under vacuum to obtain compound J.

In step 4, the compound J and $POCl_3$ were mixed in the flash at room temperature. After 10 minutes, dimethylacetamide was added dropwise and then refluxed for 16 hours. The excess $POCl_3$ was distilled out under reduced pressure and the residue was extracted with toluene and water. The toluene extract was dried over with anhydrous magnesium sulfate and concentrated under reduced pressure to generate crude compound. The crude compound (was dissolved in xylene and stirred at room temperature under nitrogen atmosphere. After 10 minutes, $R_2NH_2$ was added and then refluxed for 16 hours. The reaction mixture was poured into water. The resulting solution was alkalization by the addition of 2N aqueous solution of NaOH, and then extracted with EtOAc and water. The EtOAc extract was dried over with anhydrous magnesium sulfate and concentrated under reduced pressure. The crude product was purified by column chromatography on silica gel or aluminum oxide to obtain compound K.

In the synthesis scheme II, $R_2$ is an alkyl or an alkyl amine or alkyl aromatic ring group. The structure is defined as above.

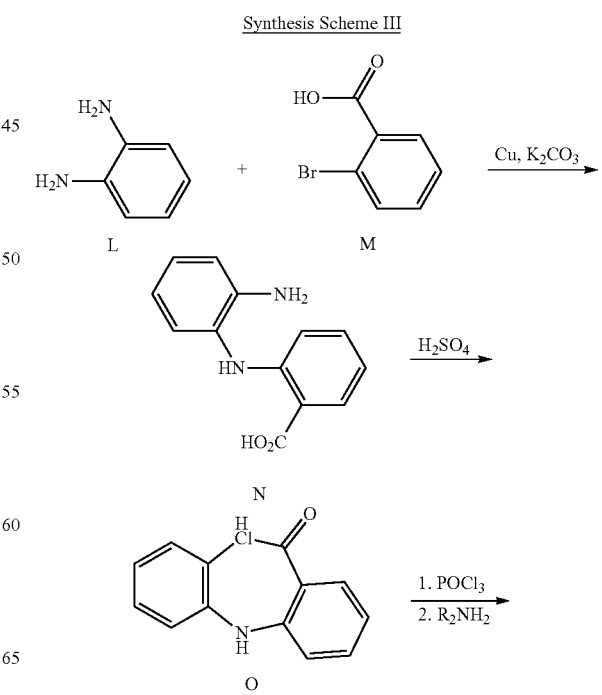

-continued

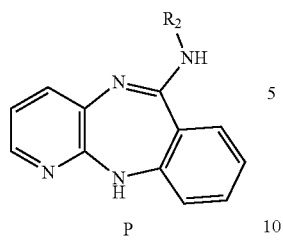

P

In the first step of synthesis scheme III, the mixture of compound L, M, copper powder and K$_2$CO$_3$ dissolved in dry N,N-dimethylformamide (DMF) was stirred for 16 hours at 170° C. under nitrogen atmosphere. The mixture was cooled to room temperature and filtered to remove the copper powder. The filtrate was concentrated under reduced pressure, and the crude product was purified by column chromatography on silica gel to obtain compound N.

In step 2, compound N in DMF was stirred with H$_2$SO$_4$ dropwise for 16 hours at 150° C. under nitrogen atmosphere. The reaction mixture was poured in cracked ice, and the precipitate were collected by filtration, washed with cold water, and dried under vacuum to obtain compound O.

In step 3, the compound O and POCl$_3$ were mixed in the flash at room temperature for 10 minutes and then refluxed for 16 hours. The excess POCl$_3$ was distilled out under reduced pressure and the residue was extracted with toluene and water. The toluene extract was dried over with anhydrous magnesium sulfate and concentrated under reduced pressure to generate crude compound. The crude compound (was dissolved in xylene and stirred at room temperature under nitrogen atmosphere. After 10 minutes, R$_2$NH$_2$ was added and then refluxed for 16 hours. The reaction mixture was poured into water. The resulting solution was alkalization by the addition of 2N aqueous solution of NaOH, and then extracted with EtOAc and water. The EtOAc extract was dried over with anhydrous magnesium sulfate and concentrated under reduced pressure. The crude product was purified by column chromatography on silica gel or aluminum oxide to obtain compound P.

In the synthesis scheme III, R$_2$ is an alkyl or an alkyl amine or alkyl aromatic ring group. The structure is defined as above.

Synthesis Scheme IV

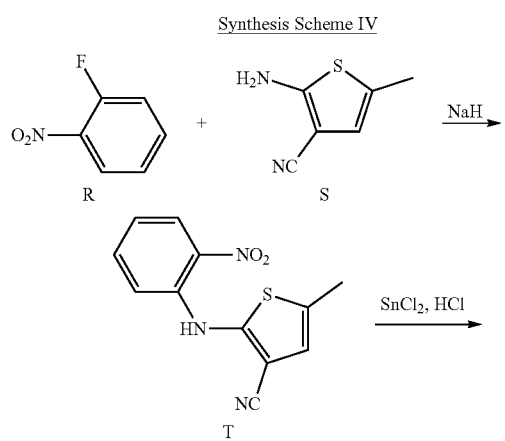

-continued

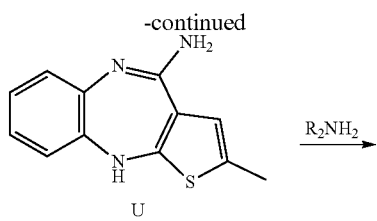

U

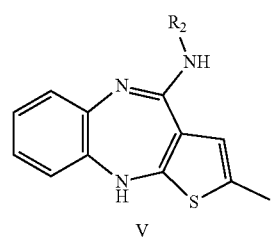

V

In the first step of synthesis scheme IV, a solution of compound R and S in dry THF was added dropwise under nitrogen atmosphere to a stirred suspension of NaH in dry THF in an ice bath. The mixture was stirred at room temperature for 16 hours, and then poured into cold water. After adjusted pH value to neutral with 20% aqueous solution of HCl, the resulting solution was extracted with EtOAc. The EtOAc extract was dried over with anhydrous magnesium sulfate and concentrated under reduced pressure. The crude product was purified by column chromatography on silica gel to obtain compound T.

In step 2, a stirred suspension of compound T in ethanol was added a solution of stannous SnCl$_2$ in concentrated HCl. The reaction mixture was stirred under reflux for 3 hours, and then concentrated under reduced pressure. Then the reaction mixture was poured in cracked ice, and the precipitate were collected by filtration, washed with cold water, and dried under vacuum to obtain compound U.

In step 3, a mixture of compound U and R$_2$NH$_2$ was stirred at 160° C. for 30 min under microwave heating in a sealed reactor tube. After cooling to room temperature, the reaction mixture was extracted with DCM and water. The DCM extract was dried over with anhydrous magnesium sulfate and concentrated under reduced pressure. The crude product was purified by column chromatography on silica gel or aluminum oxide to obtain compound V.

In the synthesis scheme IV, R$_2$ is an alkyl or an alkyl amine or alkyl aromatic ring group. The structure is defined as above.

The examples of the synthetic compounds by synthesis scheme I and bioactivity against bacterial are listed in Table 1 below.

TABLE 1

| Cpd. No. | R₂ group | EC$_{50}$ (μM) S. Typhimurium 14028 | IC$_{50}$ (μM) RAW264.7 | Selectivity ratio (IC$_{50}$/EC$_{50}$) |
|---|---|---|---|---|
| SW1 | -CH₂CH₂N(CH₃)₂ | 3.6 | 34.6 | 9.5 |
| SW2 | -(CH₂)₂-pyrrolidinyl | 4.9 | 26.6 | 5.4 |
| SW3 | -(CH₂)₂-piperidinyl | 4.3 | 22.2 | 5.1 |
| SW4 | -(CH₂)₂-morpholinyl | 32.0 | 84.7 | 2.6 |
| SW5 | -(CH₂)₂-(3-pyridyl) | 38.2 | 74.0 | 1.9 |
| SW6 | -(CH₂)₂-(1-methylpyrrolidin-2-yl) | 1.2 | 23.0 | 18.9 |
| SW7 | -(CH₂)₂-phenyl | 21.2 | 56.3 | 2.7 |
| SW8 | -(CH₂)₄CH₃ | 54.1 | 72.7 | 1.3 |
| SW9 | -CH₂-phenyl | 19.7 | 60.8 | 3.1 |
| SW10 | cyclic | N.A | N.A | N.A |

TABLE 1-continued
| Cpd. No. | R₂ group | EC$_{50}$ (μM) S. Typhimurium 14028 | IC$_{50}$ (μM) RAW264.7 | Selectivity ratio (IC$_{50}$/EC$_{50}$) |
|---|---|---|---|---|
| SW11 |  | 44.0 | 74.0 | 1.7 |
| SW12 | 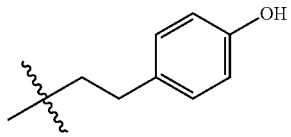 [SMILES: *CCc1ccc(O)cc1] | 33.5 | 52.1 | 1.6 |
| SW13 | 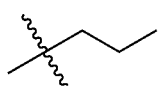 [SMILES: *CCC] | 56.0 | 111.7 | 2.0 |
| SW14 | 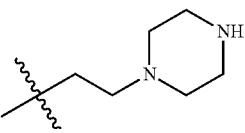 [SMILES: *CCN1CCNCC1] | 0.4 | 28.7 | 80.6 |
| SW15 | 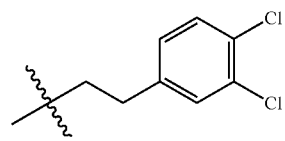 [SMILES: *CCc1ccc(Cl)c(Cl)c1] | 31.1 | 82.7 | 2.7 |
| SW16 | 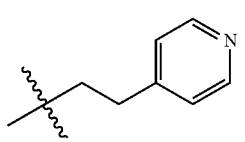 [SMILES: *CCc1ccncc1] | 18.5 | 51.1 | 2.8 |
| SW17 | 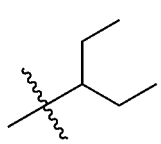 | 28.5 | 72.8 | 2.6 |
| SW18 | 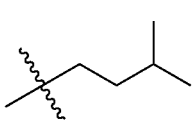 [SMILES: *CCC(C)C] | 55.1 | 70.1 | 1.3 |
| SW19 | 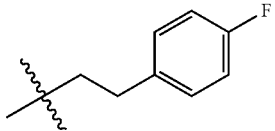 [SMILES: *CCc1ccc(F)cc1] | 61.5 | 112.2 | 1.8 |
| SW20 | 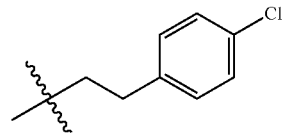 [SMILES: *CCc1ccc(Cl)cc1] | 45.1 | 91.6 | 2.0 |

TABLE 1-continued
| Cpd. No. | R₂ group | EC$_{50}$ (μM) S. Typhimurium 14028 | IC$_{50}$ (μM) RAW264.7 | Selectivity ratio (IC$_{50}$/EC$_{50}$) |
|---|---|---|---|---|
| SW22 | 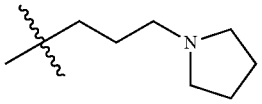 [SMILES: *CCCN1CCCC1] | 1.1 | 16.3 | 14.8 |
| SW23 | 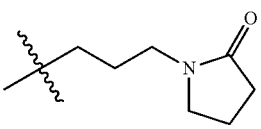 [SMILES: *CCCN1CCCC1=O] | >90 | >90 | >1.3 |
| SW24 | 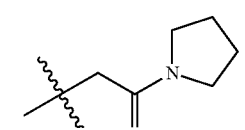 | >90 | >90 | 1.0 |
| SW26 | 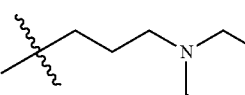 | 1.1 | 16.1 | 14.6 |
The examples of the synthetic compounds by synthesis scheme II and bioactivity against bacterial are listed in Table 2 below.
TABLE 2
| Cpd. No. | R₂ group | EC$_{50}$ (μM) S. Typhimurium 14028 | IC$_{50}$ (μM) RAW264.7 | Selectivity ratio (IC$_{50}$/EC$_{50}$) |
|---|---|---|---|---|
| SW21 | 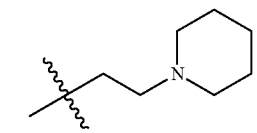 [SMILES: *CCN1CCCCC1] | 5.8 | 63.6 | 11.0 |
| SW25 | 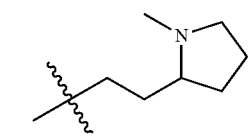 [SMILES: *CCC1CCCN1C] | 3.3 | 85.5 | 26.2 |
| SW27 | 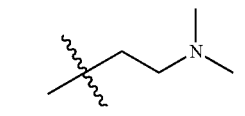 [SMILES: *CCN(C)C] | 6.5 | >90 | >13.9 |
| SW28 | 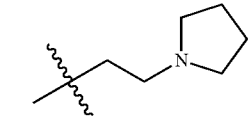 [SMILES: *CCN1CCCC1] | 9.3 | 63.2 | 6.8 |
| SW29 | 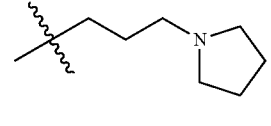 [SMILES: *CCCN1CCCC1] | 5.3 | 100.6 | 18.8 |

TABLE 2-continued

| Cpd. No. | R₂ group | EC$_{50}$ (μM) S. Typhimurium 14028 | IC$_{50}$ (μM) RAW264.7 | Selectivity ratio (IC$_{50}$/EC$_{50}$) |
| --- | --- | --- | --- | --- |
| SW30 | *propyl-piperazine-NH* | N.A | N.A | N.A |
| SW31 | *propyl-N-methylpiperazine* | 7.0 | 129.3 | 18.7 |
| SW32 | *propyl-piperidine* | 6.4 | 104.7 | 16.4 |

The examples of the synthetic compounds by synthesis scheme III and bioactivity against bacterial are listed in Table 3 below.

TABLE 3

| Cpd. No. | R₂ group | EC$_{50}$ (μM) S. Typhimurium 14028 | IC$_{50}$ (μM) RAW264.7 | Selectivity ratio (IC$_{50}$/EC$_{50}$) |
| --- | --- | --- | --- | --- |
| SW33 | *propyl-pyrrolidine* | 0.7 | 143.0 | 213.4 |
| SW35 | *propyl-piperidine* | 3.8 | 111.3 | 29.3 |

The examples of the synthetic compounds by synthesis scheme IV and bioactivity against bacterial are listed in Table 4 below.

TABLE 4

| Cpd. No. | R₂ group | EC$_{50}$ (μM) S. Typhimurium 14028 | IC$_{50}$ (μM) RAW264.7 | Selectivity ratio (IC$_{50}$/EC$_{50}$) |
| --- | --- | --- | --- | --- |
| SW38 | *ethyl-piperidine* | 1.6 | 36.5 | 22.4 |
| SW39 | *ethyl-N,N-dimethylamine* | 1.7 | 121.6 | 72.5 |

TABLE 4-continued

| Cpd. No. | R₂ group | EC$_{50}$ (μM) S. Typhimurium 14028 | IC$_{50}$ (μM) RAW264.7 | Selectivity ratio (IC$_{50}$/EC$_{50}$) |
|---|---|---|---|---|
| SW41 | 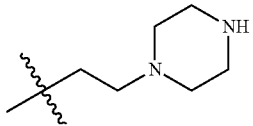 [SMILES: *CCN1CCNCC1] | 3.9 | 104.6 | 26.8 |
| SW42 | 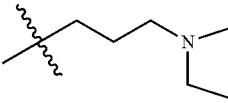 | 0.9 | 76.4 | 82.6 |
| SW43 | 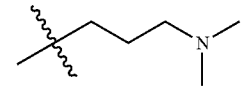 [SMILES: *CCCN(C)C] | 1.2 | 101.8 | 82.1 |

The spectral data of the above synthetic compounds are listed below.

N1-(2-chlorodibenzo[b,f][1,4]oxazepin-11-yl)-N2, N2-dimethylethane-1,2-diamine (SW1)

1H NMR (400 MHz, CDCl$_3$-d) δ 7.39 (s, 1H), 7.36 (d, J=8.8 Hz, 1H), 7.13 (d, J=8.8 Hz, 2H), 7.06 (t, J=7.6 Hz, 2H), 6.92 (t, J=7.6 Hz, 1H), 5.50 (brs, 1H), 3.58 (brs, 2H), 2.58 (t, J=6.0 Hz, 2H), 2.27 (s, 6H) ppm. 13C NMR (100 MHz, CDCl$_3$-d) δ 159.53, 155.69, 151.89, 141.27, 132.58, 130.58, 127.73, 127.50, 127.28, 126.03, 123.90, 122.48, 120.49, 57.62, 45.38, 39.09 ppm. HRMS calculated for C17H18ON3Cl (M+H)+: 316.1211. Found: 316.1213.

2-chloro-N-(2-(pyrrolidin-1-yl)ethyl)dibenzo[b,f][1,4]oxazepin-11-amine (SW2)

1H NMR (400 MHz, CDCl$_3$-d) δ 7.39 (s, 1H), 7.36 (d, J=8.8 Hz, 1H), 7.13 (d, J=8.8 Hz, 2H), 7.06 (t, J=7.6 Hz, 2H), 6.92 (t, J=7.2 Hz, 1H), 5.50 (brs, 1H), 3.61 (s, 2H), 2.77 (brs, 2H), 2.56 (s, 4H), 1.78 (s, 4H) ppm. 13C NMR (100 MHz, CDCl$_3$-d) δ 159.51, 155.78, 151.91, 141.24, 132.57, 130.57, 127.73, 127.63, 127.27, 126.03, 123.89, 122.46, 120.49, 54.55, 54.09, 40.47, 23.70 ppm. HRMS calculated for C19H20ON3Cl (M+H)+: 342.1368. Found: 342.1371.

2-chloro-N-(2-(piperidin-1-yl)ethyl)dibenzo[b,f][1,4]oxazepin-11-amine (SW3)

1H NMR (400 MHz, CDCl$_3$-d) δ 7.38-7.35 (m, 2H), 7.15-7.12 (m, 2H), 7.05 (t, J=7.6 Hz, 2H), 6.92 (t, J=7.6 Hz, 1H), 5.60 (brs, 1H), 3.58 (s, 2H), 2.61-2.60 (m, 2H), 2.43 (brs, 4H), 1.57-1.56 (m, 4H), 1.44 (s, 2H) ppm. 13C NMR (100 MHz, CDCl$_3$-d) δ 159.48, 155.63, 151.87, 141.31, 132.55, 130.62, 127.85, 127.47, 127.31, 126.03, 123.85, 122.52, 120.49, 56.90, 54.47, 38.37, 26.26, 24.66 ppm. HRMS calculated for C20H22ON3Cl (M+H)+: 356.1524. Found: 356.1528.

2-chloro-N-(2-morpholinoethyl)dibenzo[b,f][1,4]oxazepin-11-amine (SW4)

1H NMR (400 MHz, CDCl$_3$-d) δ 7.39-7.37 (m, 2H), 7.16-7.04 (m, 4H), 6.93 (t, J=7.6 Hz, 1H), 5.41 (brs, 1H), 3.72 (t, J=4.4 Hz, 4H), 3.61 (q, J=4.4 Hz, 2H), 2.67 (t, J=6.0 Hz, 2H), 2.51 (brs, 4H) ppm. 13C NMR (100 MHz, CDCl$_3$-d) δ 159.50, 155.54, 151.84, 141.13, 132.68, 130.65, 127.70, 127.35, 127.29, 126.07, 124.05, 122.60, 120.52, 67.20, 56.84, 53.56, 37.95 ppm. HRMS calculated for C19H20O2N3Cl (M+H)+: 358.1317. Found: 358.1325.

2-chloro-N-(2-(pyridin-3-yl)ethyl)dibenzo[b,f][1,4]oxazepin-11-amine (SW5)

1H NMR (400 MHz, CDCl$_3$-d) δ 8.53 (s, 1H), 8.48 (d, J=4.0 Hz, 1H), 7.60 (d, J=8.0 Hz, 1H), 7.35 (d, J=8.4 Hz, 1H), 7.26-7.24 (m, 2H), 7.14 (t, J=7.2 Hz, 2H), 7.10-7.07 (m, 2H), 6.95 (t, J=7.2 Hz, 1H), 4.80 (brs, 1H), 3.80 (q, J=6.4 Hz, 2H), 3.06 (t, J=6.8 Hz, 2H) ppm. 13C NMR (100 MHz, CDCl$_3$-d) δ 159.58, 155.05, 151.81, 150.45, 148.23, 140.96, 136.61, 135.05, 132.80, 130.69, 127.42, 127.35, 127.07, 126.10, 124.27, 123.72, 122.65, 120.56, 42.76, 32.53 ppm. HRMS calculated for C20H16ON3Cl (M+H)+: 350.1055. Found: 350.1059.

2-chloro-N-(2-(1-methylpyrrolidin-2-yl)ethyl)dibenzo[b,f][1,4]oxazepin-11-amine (SW6)

1H NMR (400 MHz, CDCl$_3$-d) δ 7.35-7.32 (m, 2H), 7.12 (d, J=8.0 Hz, 2H), 7.07-6.99 (m, 3H), 6.90 (t, J=7.6 Hz, 1H), 3.74-3.72 (m, 1H), 3.55-3.54 (m, 1H), 3.04-3.02 (m, 1H), 2.42 (brs, 1H), 2.36 (s, 3H), 2.17 (q, J=8.0 Hz, 1H), 1.92-1.90 (m, 2H), 1.84-1.75 (m, 4H) ppm. 13C NMR (100 MHz, CDCl$_3$-d) δ 159.50, 155.51, 151.88, 141.54, 132.31, 130.45, 128.08, 127.34, 127.29, 126.00, 123.60, 122.47, 120.48, 65.25, 57.25, 40.83, 39.13, 29.10, 28.64, 22.74 ppm. HRMS calculated for C20H22ON3Cl (M+H)+: 356.1524. Found: 356.1515.

2-chloro-N-phenethyldibenzo[b,f][1,4]oxazepin-11-amine (SW7)

1H NMR (400 MHz, CDCl$_3$-d) δ 7.35-7.06 (m, 11H), 6.94 (t, J=7.2 Hz, 1H), 4.69 (brs, 1H), 3.80 (q, J=6.4 Hz, 2H), 3.04 (t, J=6.8 Hz, 2H) ppm. 13C NMR (100 MHz, CDCl3-d) δ 159.54, 155.16, 151.84, 141.15, 139.51, 132.66, 130.62, 129.11, 128.91, 127.62, 127.37, 127.16, 126.76, 126.06, 124.07, 122.57, 120.52, 42.95, 35.20 ppm. HRMS calculated for C21H$_{17}$ON2Cl (M+H)+: 349.1102. Found: 349.1103.

2-chloro-N-pentyldibenzo[b,f][1,4]oxazepin-11-amine (SW8)

1H NMR (400 MHz, CDCl$_3$-d) δ 7.35 (s, 2H), 7.13 (d, J=7.6 Hz, 2H), 7.07-7.06 (m, 2H), 6.92 (t, J=7.2 Hz, 1H), 4.67 (brs, 1H), 3.51 (s, 2H), 1.70-1.67 (m, 3H), 1.40 (brs, 4H), 0.93 (brs, 3H) ppm. 13C NMR (100 MHz, CDCl$_3$-d) δ 159.61, 155.49, 151.87, 141.23, 132.60, 130.60, 127.78, 127.30, 127.19, 126.04, 123.92, 122.57, 120.47, 42.01, 29.56, 29.14, 22.69, 14.24 ppm. HRMS calculated for C18H19ON2Cl (M+H)+: 315.1259. Found: 315.1260.

N-benzyl-2-chlorodibenzo[b,f][1,4]oxazepin-11-amine (SW9)

1H NMR (400 MHz, CDCl$_3$-d) δ 7.45-7.29 (m, 7H), 7.16 (brs, 2H), 7.08 (t, J=7.6 Hz, 2H), 6.96 (t, J=7.6 Hz, 1H), 4.94 (brs, 1H), 4.72 (s, 2H) ppm. 13C NMR (100 MHz, CDCl3-d) δ 159.63, 155.15, 151.91, 140.96, 138.69, 132.81, 130.68, 129.01, 128.54, 127.85, 127.43, 127.37, 127.18, 126.10, 124.26, 122.65, 120.55, 46.28 ppm. HRMS calculated for C20H15ON2Cl (M+H)+: 335.0946. Found: 335.0936.

2-chloro-11-(piperidin-1-yl)dibenzo[b,f][1,4]oxazepine (SW10)

1H NMR (400 MHz, CDCl$_3$-d) δ 7.35 (d, J=8.8 Hz, 1H), 7.29 (s, 1H), 7.16-7.11 (m, 2H), 7.08-7.03 (m, 2H), 6.94 (t, J=7.6 Hz, 1H), 3.46 (s, 4H), 1.68 (s, 6H) ppm. 13C NMR (100 MHz, CDCl$_3$-d) δ 159.55, 159.37, 152.07, 140.70, 132.45, 130.33, 129.30, 127.24, 125.93, 125.73, 124.28, 122.77, 120.19, 48.70, 26.05, 25.10 ppm. HRMS calculated for C18H17ON2Cl (M+H)+: 313.1102. Found: 313.1103.

2-chloro-N-(cyclopropylmethyl)dibenzo[b,f][1,4]oxazepin-11-amine (SW11)

1H NMR (400 MHz, CDCl$_3$-d) δ 7.41 (s, 1H), 7.37 (d, J=8.8 Hz, 1H), 7.15-7.04 (m, 4H), 6.93 (t, J=7.2 Hz, 1H), 4.84 (s, 1H), 3.37 (s, 2H), 1.15-1.13 (m, 1H), 0.58 (d, J=6.8 Hz, 2H), 0.30 (s, 2H) ppm. 13C NMR (100 MHz, CDCl$_3$-d) δ 159.64, 155.46, 151.90, 141.20, 132.64, 130.62, 127.71, 127.29, 126.05, 123.98, 122.57, 120.49, 47.16, 10.60, 3.83 ppm. HRMS calculated for C17H15ON2Cl (M+H)+: 299.0946. Found: 299.0949.

4-(2-((2-chlorodibenzo[b,f][1,4]oxazepin-11-yl)amino)ethyl)phenol (SW12)

1H NMR (400 MHz, CDCl$_3$-d) δ 7.34 (d, J=8.8 Hz, 1H), 7.21 (s, 1H), 7.17-7.11 (m, 4H), 7.06 (brs, 2H), 6.94 (t, J=7.6 Hz, 1H), 6.78 (d, J=8.0 Hz, 2H), 4.97 (brs, 1H), 4.68 (brs, 1H), 3.76-3.75 (m, 2H), 2.95 (t, J=7.2 Hz, 2H) ppm. 13C NMR (100 MHz, CDCl3-d) δ 159.56, 155.31, 154.49, 151.89, 141.08, 132.69, 131.47, 130.64, 130.20, 127.62, 127.32, 127.18, 126.08, 124.11, 122.58, 120.53, 115.75, 43.16, 34.30 ppm. HRMS calculated for C21H17O2N2Cl (M+H)+: 365.1051. Found: 365.1057.

2-chloro-N-propyldibenzo[b,f][1,4]oxazepin-11-amine (SW13)

1H NMR (400 MHz, CDCl$_3$-d) δ 7.36-7.35 (m, 2H), 7.14 (d, J=8.8 Hz, 2H), 7.06 (t, J=7.2 Hz, 2H), 6.92 (t, J=7.6 Hz, 1H), 4.69 (brs, 1H), 3.49 (q, J=5.6 Hz, 2H), 1.72 (sextet, J=7.2 Hz, 2H), 1.03 (t, J=7.2 Hz, 3H) ppm. 13C NMR (100 MHz, CDCl$_3$-d) δ 159.62, 155.50, 151.88, 141.24, 132.60, 130.61, 127.80, 127.30, 127.18, 126.05, 123.93, 122.58, 120.48, 43.74, 22.69, 11.94 ppm. HRMS calculated for C16H15ON2Cl (M+H)+: 287.0946. Found: 287.0950.

2-chloro-N-(2-(piperazin-1-yl)ethyl)dibenzo[b,f][1,4]oxazepin-11-amine (SW14)

1H NMR (400 MHz, CDCl$_3$-d) δ 7.38-7.36 (m, 2H), 7.13 (t, J=7.2 Hz, 2H), 7.06 (t, J=7.2 Hz, 2H), 6.93 (t, J=7.2 Hz, 1H), 5.50 (brs, 1H), 3.60 (brs, 2H), 2.89 (s, 4H), 2.65 (brs, 2H), 2.48 (s, 4H) ppm. 13C NMR (100 MHz, CDCl$_3$-d) δ 159.48, 155.56, 151.84, 141.20, 132.61, 130.62, 127.76, 127.39, 127.29, 126.04, 123.95, 122.55, 120.50, 56.87, 54.39, 46.33, 38.05 ppm. HRMS calculated for C19H21ON4Cl (M+H)+: 357.1477. Found: 357.1484.

2-chloro-11-(3-(3,4-dichlorophenyl)propyl)dibenzo[b,f][1,4]oxazepine (SW15)

1H NMR (400 MHz, CDCl$_3$-d) δ 7.38-7.36 (brs, 3H), 7.24 (s, 1H), 7.17-7.07 (m, 5H), 6.97 (t, J=7.2 Hz, 1H), 4.75 (brs, 1H), 3.76 (s, 2H), 3.01 (t, J=6.4 Hz, 2H) ppm. 13C NMR (100 MHz, CDCl$_3$-d) δ 159.57, 155.19, 151.85, 139.83, 132.93, 132.76, 131.05, 130.74, 128.57, 127.26, 127.16, 126.14, 124.41, 122.70, 120.59, 42.83, 34.45 ppm. HRMS calculated for C21H15ON2Cl3 (M+H)+: 417.0323. Found: 417.0327.

2-chloro-N-(2-(pyridin-4-yl)ethyl)dibenzo[b,f][1,4]oxazepin-11-amine (SW16)

1H NMR (400 MHz, CDCl$_3$-d) δ 8.50 (s, 2H), 7.36 (d, J=8.4 Hz, 1H), 7.24-7.06 (m, 7H), 6.97 (t, J=7.6 Hz, 1H), 4.92 (brs, 1H), 3.82 (t, J=6.4 Hz, 2H), 3.06 (t, J=6.8 Hz, 2H) ppm. 13C NMR (100 MHz, CDCl$_3$-d) δ 159.55, 155.18, 151.83, 150.04, 148.78, 140.62, 133.03, 132.91, 130.70, 127.25, 127.18, 126.13, 124.54, 124.42, 122.67, 120.59, 42.21, 34.68 ppm. HRMS calculated for C20H16ON3Cl (M+H)+: 350.10547. Found: 350.10550.

2-chloro-N-(pentan-3-yl)dibenzo[b,f][1,4]oxazepin-11-amine (SW17)

1H NMR (400 MHz, CDCl$_3$-d) δ 7.37-7.34 (m, 2H), 7.12 (t, J=9.2 Hz, 2H), 7.05 (t, J=7.6 Hz, 2H), 6.91 (t, J=7.6 Hz, 1H), 4.44 (brs, 1H), 4.16 (brs, 1H), 1.77-1.67 (m, 2H), 1.62-1.52 (m, 2H), 0.99 (t, J=7.6 Hz, 6H) ppm. 13C NMR (100 MHz, CDCl$_3$-d) δ 159.57, 155.10, 151.76, 141.36, 132.51, 130.55, 128.06, 127.27, 127.01, 125.98, 123.67, 122.61, 120.41, 53.14, 27.02, 10.44 ppm. HRMS calculated for C18H19ON2Cl (M+H)+: 315.1259. Found: 315.1260.

2-chloro-N-isopentyldibenzo[b,f][1,4]oxazepin-11-amine (SW18)

1H NMR (400 MHz, CDCl$_3$-d) δ 7.37-7.35 (m, 2H), 7.14 (d, J=7.6 Hz, 2H), 7.08-7.06 (m, 2H), 6.92 (t, J=7.6 Hz, 1H), 4.60 (brs, 1H), 3.54 (q, J=6.4 Hz, 2H), 1.79-1.69 (m, 1H), 1.61-1.56 (m, 2H), 0.98 (d, J=6.4 Hz, 6H) ppm. 13C NMR (100 MHz, CDCl3-d) δ 159.62, 155.47, 151.88, 141.27, 132.60, 130.61, 127.81, 127.34, 127.17, 126.05, 123.93, 122.59, 120.48, 40.27, 38.49, 26.35, 22.86 ppm. HRMS calculated for C18H19ON2Cl (M+H)+: 315.1259. Found: 315.1267.

2-chloro-N-(4-fluorophenethyl)dibenzo[b,f][1,4]oxazepin-11-amine (SW19)

1H NMR (400 MHz, CDCl₃-d) δ 7.35 (d, J=8.4 Hz, 1H), 7.24-7.21 (m, 4H), 7.16-7.12 (m, 2H), 7.07 (d, J=6.8 Hz, 2H), 7.02-6.93 (m, 3H), 4.69 (brs, 1H), 3.77 (d, J=6.0 Hz, 2H), 3.01 (t, J=6.4 Hz, 2H) ppm. 13C NMR (100 MHz, CDCl₃-d) δ 161.90 (d, J=242.9 Hz), 159.55, 155.13, 151.83, 141.07, 135.16, 132.72, 130.65, 130.47 (d, J=7.7 Hz), 127.55, 127.34, 127.10, 126.08, 124.16, 122.61, 120.54, 115.66 (d, J=21.1 Hz), 43.07, 34.43 ppm. HRMS calculated for C21H16ON2ClF (M+H)+: 367.1008. Found: 367.1009.

2-chloro-N-(4-chlorophenethyl)dibenzo[b,f][1,4]oxazepin-11-amine (SW20)

1H NMR (400 MHz, CDCl₃-d) δ 7.35 (d, J=8.8 Hz, 1H), 7.28 (d, J=8.4 Hz, 2H), 7.22-7.16 (m, 3H), 7.13 (d, J=8.4 Hz, 2H), 7.09 (t, J=7.6 Hz, 2H), 6.95 (t, J=7.2 Hz, 1H), 4.70 (brs, 1H), 3.76 (q, J=4.4 Hz, 2H), 3.01 (t, J=7.6 Hz, 2H) ppm. 13C NMR (100 MHz, CDCl3-d) δ 159.54, 155.16, 151.83, 140.96, 137.98, 132.79, 132.54, 130.68, 130.44, 128.98, 127.44, 127.30, 127.13, 126.10, 124.24, 122.64, 120.55, 42.95, 34.61 ppm. HRMS calculated for C21H16ON2Cl2 (M+H)+: 383.0712. Found: 383.0713.

8-chloro-N-(2-(piperidin-1-yl)ethyl)-11H-benzo[e]pyrido[3,2-b][1,4]diazepin-6-amine (SW21)

1H NMR (400 MHz, CDCl₃-d) δ 7.74 (d, J=3.6 Hz, 1H), 7.29 (s, 2H), 7.22 (brs, 1H), 6.88 (t, J=6.4 Hz, 1H), 6.75 (d, J=8.4 Hz, 1H), 5.87 (s, 1H), 5.59 (brs, 1H), 3.54 (brs, 2H), 2.58 (t, J=6.0 Hz, 2H), 2.42 (brs, 4H), 1.58-1.55 (m, 4H), 1.44 (brs, 2H) ppm. 13C NMR (100 MHz, CDCl₃-d) δ 157.91, 152.24, 149.14, 141.36, 135.78, 134.61, 132.08, 128.01, 127.91, 127.20, 121.37, 120.57, 56.86, 54.46, 38.80, 26.27, 24.65 ppm. HRMS calculated for C19H22N5Cl (M+H)+: 356.1636. Found: 356.1626.

2-chloro-N-(3-(pyrrolidin-1-yl)propyl)dibenzo[b,f][1,4]oxazepin-11-amine (SW22)

1H NMR (400 MHz, CDCl₃-d) δ 7.88 (brs, 1H), 7.33 (d, J=8.8 Hz, 1H), 7.30 (s, 1H), 7.12 (d, J=8.0 Hz, 2H), 7.05 (t, J=8.0 Hz, 2H), 6.89 (t, J=7.2 Hz, 1H), 3.63 (s, 2H), 2.72 (brs, 2H), 2.54 (s, 4H), 1.86 (brs, 2H), 1.74 (s, 4H) ppm. 13C NMR (100 MHz, CDCl3-d) δ 159.56, 155.79, 151.93, 141.71, 132.24, 130.33, 128.27, 127.23, 127.20, 125.99, 123.43, 122.45, 120.45, 56.37, 54.30, 43.32, 25.73, 23.57 ppm. HRMS calculated for C20H22ON3Cl (M+H)+: 356.1524. Found: 356.1533.

1-(3-((2-chlorodibenzo[b,f][1,4]oxazepin-11-yl)amino)propyl)pyrrolidin-2-one (SW23)

1H NMR (400 MHz, CDCl₃-d) δ 7.52 (s, 1H), 7.34 (d, J=8.8 Hz, 1H), 7.12-7.02 (m, 4H), 6.90 (t, J=7.4 Hz, 1H), 5.97 (brs, 1H), 3.51 (q, J=5.6 Hz, 2H), 3.42 (s, 4H), 2.39 (t, J=7.6 Hz, 2H), 2.04 (qui, J=7.2 Hz, 2H), 1.91—1.88 (m, 2H) ppm. 13C NMR (100 MHz, CDCl3-d) δ 176.08, 159.35, 155.34, 151.81, 141.35, 132.53, 130.77, 127.76, 127.54, 127.09, 125.92, 123.66, 122.31, 120.45, 47.54, 40.10, 37.81, 31.14, 25.81, 18.16 ppm. HRMS calculated for C20H20O2N3Cl (M+H)+: 370.1317. Found: 370.1304.

2-((2-chlorodibenzo[b,f][1,4]oxazepin-11-yl)amino)-1-(pyrrolidin-1-yl)ethan-1-one (SW24)

1H NMR (400 MHz, CDCl₃-d) δ 7.49 (s, 1H), 7.37 (d, J=8.4 Hz, 1H), 7.14-7.04 (m, 4H), 6.94 (t, J=7.6 Hz, 1H), 6.07 (s, 1H), 4.24 (s, 2H), 3.55 (t, J=6.8 Hz, 2H), 3.50 (t, J=6.8 Hz, 2H), 2.02 (qui, J=6.4 Hz, 2H), 1.91 (qui, J=6.4 Hz, 2H) ppm. 13C NMR (100 MHz, CDCl₃-d) δ 167.19, 159.52, 155.00, 151.99, 141.03, 132.82, 130.85, 127.61, 127.30, 127.23, 126.03, 124.22, 122.43, 120.65, 46.27, 45.78, 44.28, 26.17, 24.42 ppm. HRMS calculated for C19H18O2N3Cl (M+H)+: 356.1160. Found: 356.1165.

8-chloro-N-(2-(1-methylpyrrolidin-2-yl)ethyl)-11H-benzo[e]pyrido[3,2-b][1,4]diazepin-6-amine (SW25)

1H NMR (400 MHz, CDCl₃-d) δ 7.72 (dd, J=4.8, 1.6 Hz, 1H), 7.29 (dd, J=7.6, 1.6 Hz, 1H), 7.24 (s, 1H), 7.20 (dd, J=8.8, 2.0 Hz, 1H), 7.11 (brs, 1H), 6.88 (dd, J=7.6, 4.8 Hz, 1H), 6.73 (d, J=8.8 Hz, 1H), 5.89 (s, 1H), 3.70— 3.65 (m, 1H), 3.54-3.46 (m, 1H), 3.05-3.01 (m, 1H), 2.44-2.38 (m, 1H), 2.35 (s, 3H), 2.16 (q, J=8.4 Hz, 1H), 1.96-1.87 (m, 2H), 1.82-1.72 (m, 4H) ppm. 13C NMR (100 MHz, CDCl₃-d) δ 157.78, 152.22, 149.07, 141.10, 136.02, 134.52, 131.84, 127.85, 127.71, 127.36, 121.23, 120.52, 65.20, 57.21, 40.80, 39.51, 28.84, 28.50, 22.77 ppm. HRMS calculated for C19H22N5Cl (M+H)+: 356.1636. Found: 356.1650.

2-chloro-N-(3-(piperidin-1-yl)propyl)dibenzo[b,f][1,4]oxazepin-11-amine (SW26)

1H NMR (400 MHz, CDCl₃-d) δ 7.85 (brs, 1H), 7.44 (s, 1H), 7.34 (d, J=8.4 Hz, 1H), 7.13 (d, J=9.6 Hz, 2H), 7.05 (t, J=8.0 Hz, 2H), 6.90 (t, J=7.6 Hz, 1H), 3.62 (brs, 2H), 2.55-2.42 (m, 6H), 1.84-1.81 (m, 2H), 1.49 (s, 4H), 1.41 (s, 2H) ppm. 13C NMR (100 MHz, CDCl3-d) δ 159.60, 155.95, 151.95, 141.73, 132.28, 130.37, 128.09, 127.75, 127.26, 126.00, 123.43, 122.38, 120.46, 59.66, 54.95, 43.49, 26.10, 24.47, 23.66 ppm. HRMS calculated for C21H24ON3Cl (M+H)+: 370.1681. Found: 370.1693.

N1-(8-chloro-11H-benzo[e]pyrido[3,2-b][1,4]diazepin-6-yl)-N2,N2-dimethylethane-1,2-diamine (SW27)

1H NMR (400 MHz, MeOD-d4) δ 7.80 (d, J=4.4 Hz, 1H), 7.51 (s, 1H), 7.39 (d, J=8.8 Hz, 1H), 7.34 (d, J=8.0 Hz, 1H), 7.03-6.98 (m, 2H), 3.82 (t, J=5.2 Hz, 2H), 3.43 (t, J=5.2 Hz, 2H), 2.99 (s, 6H) ppm. 13C NMR (100 MHz, CDCl₃-d) δ 158.04, 152.46, 148.85, 141.93, 134.97, 134.46, 132.61, 128.65, 128.49, 126.07, 121.34, 120.44, 58.01, 44.46, 37.96 ppm. HRMS calculated for C16H18N5Cl (M+H)+: 316.1323. Found: 316.1334.

8-chloro-N-(2-(pyrrolidin-1-yl)ethyl)-11H-benzo[e]pyrido[3,2-b][1,4]diazepin-6-amine (SW28)

1H NMR (400 MHz, CDCl₃-d) δ 7.75 (d, J=4.8 Hz, 1H), 7.48 (s, 1H), 7.24-7.22 (m, 2H), 6.88 (dd, J=7.6, 4.8 Hz, 1H), 6.73 (d, J=8.4 Hz, 1H), 5.86 (s, 1H), 3.84 (t, J=5.6 Hz, 2H), 3.21 (brs, 2H), 3.11 (brs, 4H), 2.02 (brs, 4H) ppm. 13C NMR (100 MHz, CDCl3-d) δ 157.99, 152.44, 148.92, 141.77, 135.25, 134.47, 132.48, 128.49, 128.40, 126.32, 121.31, 120.45, 55.12, 54.60, 39.29, 23.64 ppm. HRMS calculated for C18H20N5Cl (M+H)+: 342.1480. Found: 342.1493.

8-chloro-N-(3-(pyrrolidin-1-yl)propyl)-11H-benzo[e]pyrido[3,2-b][1,4]diazepin-6-amine (SW29)

1H NMR (400 MHz, MeOD) δ 7.71 (dd, J=4.8, 1.6 Hz, 1H), 7.37 (d, J=2.4 Hz, 1H), 7.34-7.29 (m, 2H), 6.98-6.93 (m, 2H), 3.49 (t, J=6.8 Hz, 2H), 2.69-2.63 (m, 6H), 1.97-

1.90 (m, 2H), 1.83-1.79 (m, 4H). 13C NMR (100 MHz, CDCl$_3$) δ 157.84, 152.10, 148.88, 140.67, 135.91, 134.15, 131.56, 127.43, 127.42, 127.35, 121.01, 120.29, 56.17, 54.06, 43.58, 25.37, 23.30. HRMS calculated for C19H22N5Cl [M+H]+: 356.1636. Found: 356.1637.

8-chloro-N-(2-(piperazin-1-yl)ethyl)-11H-benzo[e]pyrido[3,2-b][1,4]diazepin-6-amine (SW30)

1H NMR (400 MHz, MeOD-d4) δ 8.15 (d, J=4.0 Hz, 1H), 7.77 (d, J=8.0 Hz, 1H), 7.73 (s, 1H), 7.62 (d, J=8.4 Hz, 1H), 7.23-7.17 (m, 2H), 3.92 (t, J=6 Hz, 2H), 3.39 (t, J=6 Hz, 2H), 3.12 (brs, 6H). 13C NMR (100 MHz, MeOD-d4) δ 163.83, 156.05, 150.65, 147.36, 136.82, 134.84, 131.69, 129.76, 124.89, 124.02, 121.22, 120.29, 55.89, 50.51, 43.99, 41.61. HRMS calculated for C18H21N6Cl [M+H]+: 357.1589. Found: 357.1589.

8-chloro-N-(3-(4-methylpiperazin-1-yl)propyl)-11H-benzo[e]pyrido[3,2-b][1,4]diazepin-6-amine (SW31)

1H NMR (400 MHz, CDCl$_3$) δ 7.69 (d, J=4.8 Hz, 1H), 7.45 (s, 1H), 7.26 (s, 1H), 7.20-7.18 (m, 1H), 6.84 (dd, J=7.2, 4.8 Hz, 1H), 6.72 (d, J=8.4 Hz, 1H), 5.89 (s, 1H), 3.55 (q, J=5.2 Hz, 2H), 2.53-2.19 (m, 13H), 1.79-1.74 (m, 2H). 13C NMR (100 MHz, CDCl3) δ 158.02, 152.12, 149.07, 140.75, 135.84, 134.22, 131.67, 127.92, 127.27, 127.22, 121.09, 120.31, 58.80, 54.85, 53.33, 45.68, 43.72, 23.38. HRMS calculated for C10H25N6Cl [M+H]+: 385.1902. Found: 385.1902.

8-chloro-N-(3-(piperidin-1-yl)propyl)-11H-benzo[e]pyrido[3,2-b][1,4]diazepin-6-amine (SW32)

1H NMR (400 MHz, MeOD-d4) δ 7.71 (d, J=3.2 Hz, 1H), 7.40 (s, 1H), 7.34-7.30 (m, 2H), 6.99-6.95 (m, 2H), 3.49 (t, J=6.8 Hz, 2H), 2.52-2.50 (m, 6H), 2.52-2.50 (m, 2H), 1.58 (brs, 4H), 1.47 (brs, 2H). 13C NMR (100 MHz, MeOD-d4) δ 160.45, 154.47, 150.87, 141.74, 137.25, 135.31, 133.01, 129.33, 128.59, 128.11, 122.47, 121.14, 58.63, 55.51, 42.04, 26.55, 26.17, 25.15.

N-(3-(pyrrolidin-1-yl)propyl)-5H-dibenzo[b,e][1,4]diazepin-11-amine (SW33)

1H NMR (400 MHz, MeOD-d4) δ 7.36 (d, J=7.6 Hz, 1H), 7.29 (t, J=7.6 Hz, 1H), 7.02-6.85 (m, 4H), 6.85-6.77 (m, 2H), 3.50 (t, J=6.4 Hz, 2H), 2.68 (t, J=7.2 Hz, 2H), 2.62 (brs, 4H), 1.98-1.91 (m, 2H), 1.80 (brs, 4H). 13C NMR (100 MHz, CDCl$_3$) δ 158.68, 152.90, 141.64, 141.04, 131.44, 127.77, 127.07, 126.58, 124.19, 122.62, 122.38, 119.27, 119.07, 55.70, 54.04, 42.59, 26.37, 23.37.

N-(2-(piperidin-1-yl)ethyl)-5H-dibenzo[b,e][1,4]diazepin-11-amine (SW35)

1H NMR (400 MHz, MeOD-d4) δ 7.38 (d, J=7.6 Hz, 1H), 7.28 (t, J=7.6 Hz, 1H), 6.99-6.81 (m, 6H), 3.60 (t, J=6.8 Hz, 2H), 2.69 (t, J=6.4 Hz, 2H), 2.54 (s, 4H), 1.63-1.61 (m, 4H), 1.48 (brs, 2H). 13C NMR (100 MHz, MeOD-d4) δ 158.58, 152.81, 141.11, 141.07, 131.70, 127.94, 127.02, 126.09, 124.22, 123.00, 122.85, 119.39, 119.29, 56.96, 54.22, 38.37, 25.93, 24.33. HRMS calculated for C20H24N4 [M+H]+: 321.2070. Found: 321.2074.

2-methyl-N-(2-(piperidin-1-yl)ethyl)-10H-benzo[b]thieno[2,3-e][1,4]diazepin-4-amine (SW38)

1H NMR (400 MHz, MeOD-d4) δ 6.90-6.84 (m, 2H), 6.66 (d, J=7.2 Hz, 1H), 6.53 (brs, 1H), 3.57 (t, J=6.4 Hz, 2H), 2.68 (t, J=6.4 Hz, 2H), 2.58 (brs, 4H), 2.30 (s, 3H), 1.66—1.61 (m, 4H), 1.49 (brs, 2H). NMR (100 MHz, CDCl$_3$) δ 158.51, 157.08, 145.26, 140.94, 128.58, 128.49, 125.25, 123.06, 120.22, 118.54, 59.69, 54.27, 38.63, 26.08, 24.45, 15.25. HRMS calculated for C19H24N4S [M+H]+: 341.1793. Found: 341.1794.

N1,N1-dimethyl-N2-(2-methyl-10H-benzo[b]thieno[2,3-e][1,4]diazepin-4-yl)ethane-1,2-diamine (SW39)

1H NMR (400 MHz, MeOD-d4) δ 6.90-6.83 (m, 2H), 6.83-6.78 (m, 1H), 6.63 (d, J=7.2 Hz, 1H), 6.53 (brs, 1H), 3.53 (t, J=6.4 Hz, 2H), 2.63 (t, J=6.4 Hz, 2H), 2.32 (s, 6H), 2.28 (s, 3H). 13C NMR (100 MHz, MeOD-d4) δ 158.30, 156.87, 145.05, 140.73, 128.37, 128.29, 125.04, 122.85, 120.01, 118.34, 59.36, 48.36, 45.36, 40.18, 15.04. HRMS calculated for C19H2ON4S [M+H]+: 301.1479. Found: 301.1481.

2-methyl-N-(2-(piperazin-1-yl)ethyl)-10H-benzo[b]thieno[2,3-e][1,4]diazepin-4-amine (SW41)

1H NMR (400 MHz, MeOD-d4) δ 6.97-6.92 (m, 2H), 6.92-6.87 (m, 2H), 6.69 (d, J=7.6 Hz, 1H), 6.54 (brs, 1H), 3.58 (t, J=6 Hz, 2H), 2.85 (brs, 4H), 2.69 (t, J=6.0 Hz, 4H), 2.59 (brs, 4H), 2.29 (s, 3H). 13C NMR (100 MHz, CDCl$_3$) δ 158.58, 157.09, 145.12, 140.18, 128.58, 128.10, 125.25, 122.75, 120.17, 117.97, 56.08, 53.48, 45.38, 37.22, 15.14. HRMS calculated for C18H23N5S [M+H]+: 342.1745. Found: 342.1747.

2-methyl-N-(3-(pyrrolidin-1-yl)propyl)-10H-benzo[b]thieno[2,3-e][1,4]diazepin-4-amine (SW42)

1H NMR (400 MHz, MeOD-d4) δ 6.90-6.86 (m, 2H), 6.86-6.80 (m, 1H), 6.64 (d, J=8 Hz, 1H), 6.49 (brs, 1H), 3.46 (t, J=6.4 Hz, 2H), 2.68-2.64 (m, 6H), 2.28 (s, 3H), 1.90 (quin, J=7.2 Hz, 2H), 1.80 (brs, 4H). 13C NMR (100 MHz, CDCl$_3$) δ 158.60, 157.17, 145.35, 141.55, 128.67, 128.58, 125.34, 123.15, 120.31, 118.63, 56.94, 54.89, 44.31, 26.27, 24.14, 15.34. HRMS calculated for C19H24N4S [M+H]+: 341.1793. Found: 341.1791.

N1,N1-dimethyl-N3-(2-methyl-10H-benzo[b]thieno[2,3-e][1,4]diazepin-4-yl)propane-1,3-diamine (SW43)

1H NMR (400 MHz, MeOD-d4) δ 6.94-6.89 (m, 2H), 6.89-6.84 (m, 1H), 6.68 (d, J=7.2 Hz, 1H), 6.51 (brs, 1H), 3.44 (t, J=6.4 Hz, 2H), 2.48 (t, J=6.8 Hz, 2H), 2.28 (s, 9H), 1.88-1.85 (m, 2H). 13C NMR (100 MHz, MeOD-d4) δ 158.50, 157.01, 145.04, 140.10, 128.75, 128.02, 125.34, 125.17, 122.68, 120.10, 117.90, 57.48, 48.36, 44.99, 40.63, 27.50, 15.06.

Anti-Intracellular *Salmonella* Activity and Cytotoxicity of SW14

Figure 2:
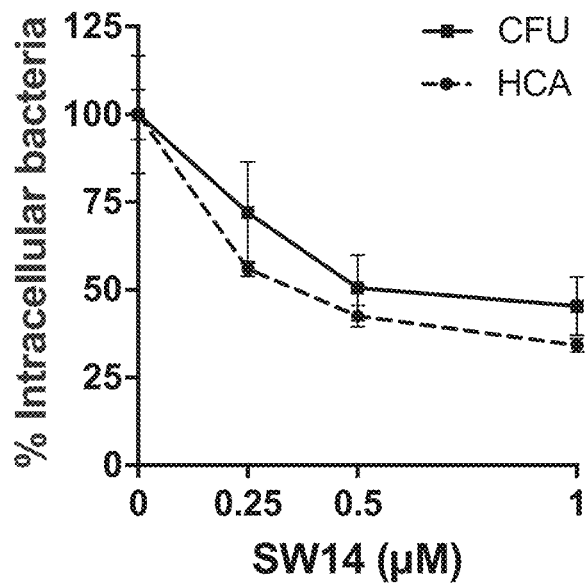
FIG. 2. Intracellular bacteria survival of S. typhimurium-infected RAW264.7 cells treated with 0, 0.25, 0.5, and 11.11\4 of SW14 in the presence of gentamicin (20 mg/L) for 24 h. The intracellular bacteria survival was assessed using HCA and a CFU assay, and the data are expressed as a percentage relative to the untreated control and are presented as the mean±SD (n=3 per group).
Figure 3:
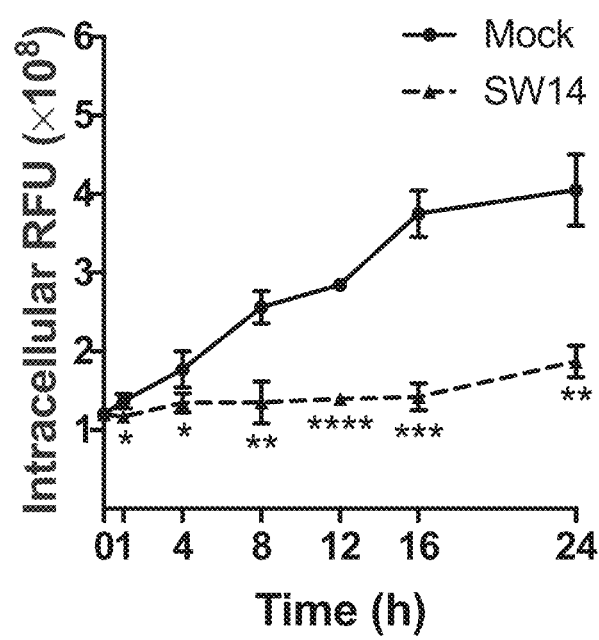
FIG. 3. S. typhimurium-infected RAW264.7 cells treated with 0.5 μM of SW14 in combination with gentamicin (20 mg/L). The relative number of intracellular bacteria was determined at 1, 4, 8, 12, 16, and 24 hours using HCA and the results are expressed as relative fluorescence units (RFU). The data are presented as the mean±SD (n=3 per group). *P<0.05; P<0.01; *P<0.001; ****P<0.0001.
Figure 4:
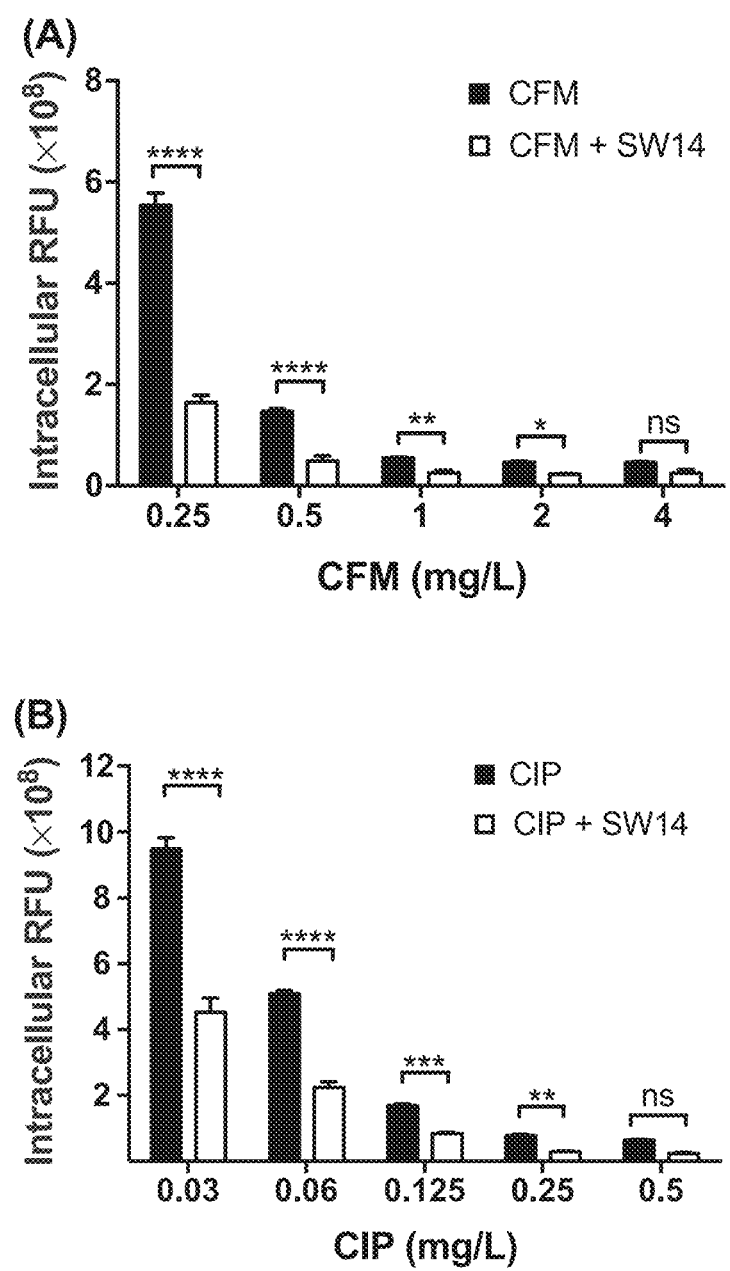
FIG. 4. Salmonella-infected RAW264.7 cells treated with (A) 0.25, 0.5, 1, 2, and 4 mg/L of cefixime (CFM) and (B) 0.03, 0.06, 0.125, 0.25, and 0.5 mg/L of ciprofloxacin (CIP) alone or in combination with 0.5 μM SW14. After 24 hours, the relative numbers of intracellular bacteria were determined using HCA and the results are expressed as relative fluorescence units (RFU). The data are presented as the mean±SD (n=3 per group). ns: non-significant, P>0.05; *P<0.05; P<0.01; *P<0.001; ****P<0.0001.

The anti-intracellular *Salmonella* activity and cytotoxicity of SW14 were confirmed by a colony-forming unit assay and MTT cell viability assay respectively, and the results are showed by FIG. 1 and FIG. 2 Consistent with the findings of HCA, SW14 exhibited a potent suppressive effect on the viability of intracellular *Salmonella* at sub-micromolar concentrations, indicating that the anti-intracellular *Salmonella* activity of SW14 observed from the HCA was not due to interference with the RFP expression Closer time-dependent examination of the effects of SW14 on intracellular *Salmonella* is showed by FIG. 3. FIG. 3 shows that there was a significant difference in the relative number of bacteria in the infected cells after treatment with SW14 for 1 hour, and the number of intracellular bacteria did not increase significantly in the subsequent time period, suggesting that SW14 acts by limiting the proliferation of intracellular *Salmonella*.

SW14 Sensitized Intracellular *Salmonella* to Ciprofloxacin and Cefixime

To observe the sensitivity-increasing of antibiotics of cefixime (CFM) and ciprofloxacin (CIP) by SW14, infected RAW264.7 cells with RFP-expressing *Salmonella* are used to experiment. The infected cells are treated with CFM, CIP or combination each of above antibiotics with SW14 for 24 hours, and the results indicated that CFM and CIP inhibited the survival of intracellular *Salmonella* in macrophages in a dose-dependent manner, especially, when the CFM and CIP are combined with 0.5 μM SW14. Therefore, the results indicate that SW14 can enhance the suppression caused by these antibiotics against intracellular *Salmonella*.

Multidrug-Resistant and Fluoroquinolone-Resistant *S. typhimurium* in Macrophages by Treated with SW14

To investigate the inhibition of drug-resistant *Salmonella* infection in cells of SW14, the RFP-expressing plasmids are transformed into two multidrug-resistant clinical isolates of *S. typhimurium*, and then evaluated the effects of SW14 on infection from these four types of multidrug-resistant strains.

Figure 5:
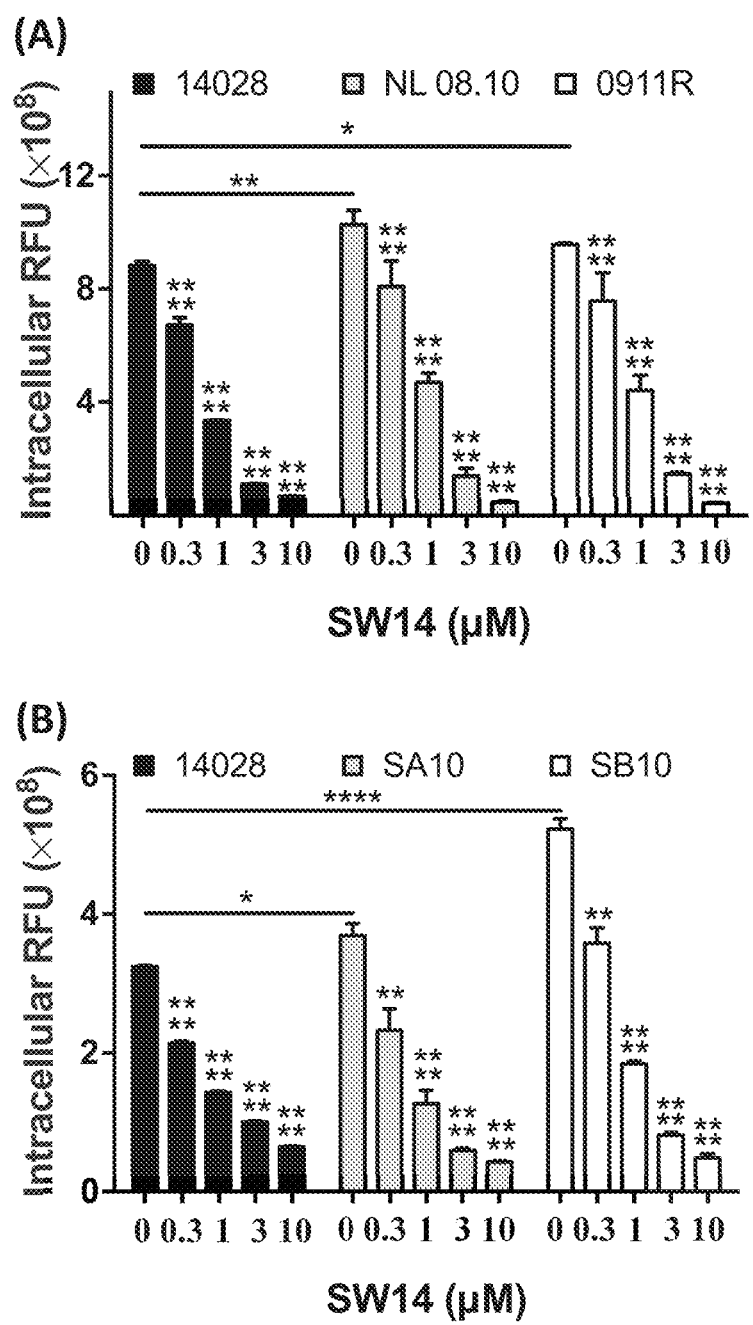
FIG. 5. RAW264.7 cells infected with (A) multidrug-resistant strains of S. Typhimurium ATCC 14028, NL08., and 100911R or (B) ciprofloxacin-resistant strains of S. typhimurium ATCC 14028, SA10, and SB10 followed by treatment with 0, 0.3, 1, 3, and 10 μM of SW14 combined with 20 mg/mL gentamicin for 24 h. The relative numbers of intracellular bacteria were determined using HCA and the results are expressed as relative fluorescence units (RFU). The data are presented as the mean±SD (n=3 per group). *P<0.05; P<0.01; **P<0.0001.

According to Table 5, compared to the *S. typhimurium* strain ATCC 14028, the multidrug-resistant *S. typhimurium* NL08.10 and 0911R isolates were highly resistant to the antibiotics. Additionally, according to FIG. 5(A), the relative numbers of bacteria in cells infected with the multidrug-resistant strains *S. typhimurium* NL08.10 and 0911R were higher than that of cells infected with the *S. typhimurium* strain ATCC 14028. Despite differences in antibiotic resistance and infectivity, the intracellular replication of the two multidrug-resistant *S. typhimurium* isolates remained susceptible to the suppressive activity of SW14.

TABLE 5

| Antibiotic | MIC (mg/L) *Salmonella Typhimurium* | | |
|---|---|---|---|
| | ATCC 14028 | NL08.10 | 0911R |
| Gentamycin | 2 | 2 | 2 |
| Tetracycline | 8 | >64 | >64 |
| Streptomycin | 32 | >64 | >64 |
| Chloramphenicol | 16 | 32 | 32 |
| Ampicillin | 16 | >64 | >64 |

Then extended the investigation to *S. typhimurium* isolates with resistance to ciprofloxacin. In Table 6, the ciprofloxacin-resistant strain SA10 and SB10 showed higher infectivity than *S. typhimurium* strain ATCC 14028. However, the intracellular proliferation of ciprofloxacin-resistant isolates was still highly sensitive to SW14. These results indicate that the antibacterial activity of SW14 is not affected by bacterial infectivity or resistance mechanisms to common antibiotics.

TABLE 6

| Antibiotic | MIC (mg/L) *Salmonella Typhimurium* | | |
|---|---|---|---|
| | ATCC 14028 | SA10 | SB10 |
| Gentamycin | 2 | 0.5 | 1 |
| Ciprofloxacin | <0.125 | 4 | 4 |
| Ofloxacin | <0.125 | 8 | 8 |

Mechanism of Action of SW14

To elucidate the mechanism of action of SW14, first examined whether SW14 can directly inhibit bacterial growth in medium by exposing bacteria to escalating concentrations of SW14 in LB medium and macrophage culture medium (DMEM supplemented with 10% FBS) followed by monitoring the density (OD600) of the bacterial cultures at different time points for 24 hours.

Figure 6:
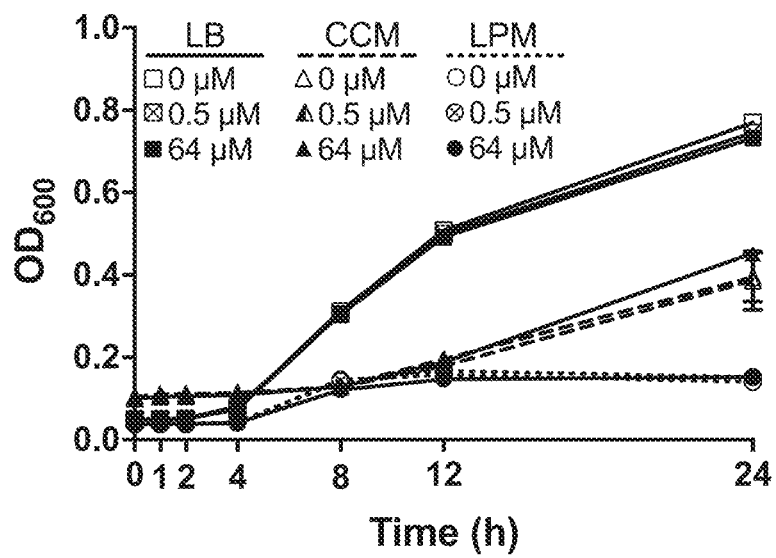
FIG. 6. The growth of S. typhimurium in LB medium, cell culture medium (CCM), or LPM medium containing 0, 0.5, and 64 μM of SW14 monitored by measuring the $OD_{600}$ of each bacterial culture at designated times for a total of 24 h. The data are presented as the mean±SD (n=3 per group).

As shown in FIG. 6, SW14 did not show significant inhibitory effects on the growth of bacteria in either medium at concentrations up to 64 NM.

Then tested the effects of SW14 on the growth of *Salmonella* in acidic LPM medium, which mimics the environment of macrophage phagosomes. Consistent with previous results show that the outer membrane of *Salmonella* is compromised in the phagosome microenvironment, the susceptibility of *Salmonella* to several antibiotics was elevated in the LPM medium according Table 7.

TABLE 7

| Antibiotic | MIC (mg/L) *S. Typhimurium* ATCC 14028 | | |
|---|---|---|---|
| | CAMH | LB | LPM |
| Vancomycin | 2048 | 512 | 128 |
| Ampicillin | 4 | 4 | 1 |
| Rifampin | 16 | 16 | 4 |

Figure 7:
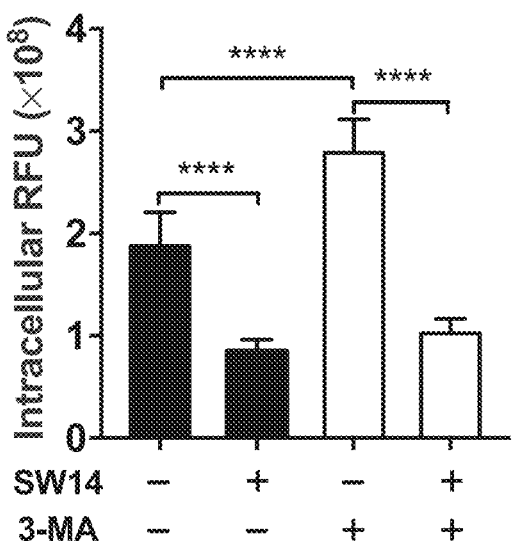
FIG. 7. Infected RAW264.7 cells treated with 10 mM of 3-MA for 1 h followed by 0.5 μM of SW14 or mock (DMSO) treatment for 24 hours. The viability of the intracellular bacteria was assessed using HCA and the results are expressed as a percentage relative to the mock-treated cells. The data are presented as the mean±SD (n=3 per group). ****P<0.0001.

Autophagy was originally characterized as a cellular response to stress, but has been considered to be a defense mechanism to combat host cell infection by intracellular *Salmonella*. Therefore, to evaluated the role of autophagy in SW14's anti-intracellular *Salmonella* activity, infected cells are treated with 3-MA, an autophagy inhibitor to block cellular autophagy then followed by treatment with SW14 for 24 h. As shown in FIG. 7, the relative number of intracellular bacteria increased significantly in 3-MA-treated cells, suggesting that autophagic defense was inhibited. Compared to mock-treated cells, the viability of intracellular *Salmonella* in cells treated with SW14 or the combination of 3-MA and SW14 were 45% and 36.8%, respectively.

Figure 8:
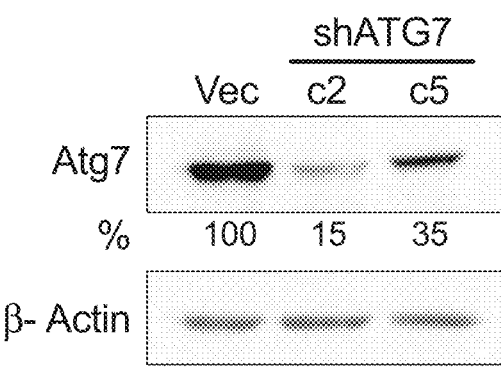
FIG. 8. RAW264.7 cells transfected with a plasmid to express shRNA targeting Atg7 (shATG7). The levels of the Atg7 protein in the stable transfectants as determined by immunoblotting. Bands for Atg7 were quantified by densitometry and normalized to those of β-actin. Percentages represent the relative expression levels of Atg7 in the shATG7 transfectants compared to the vector transfectants.

Next, further employed shRNA to knockdown the expression of Atg7, a key protein involved in autophagosome formation, obtaining two clones of RAW264.7 cells with Atg7 levels of 15% and 35% that of the cells transfected with empty vector as shows in FIG. 8.

Figure 9:
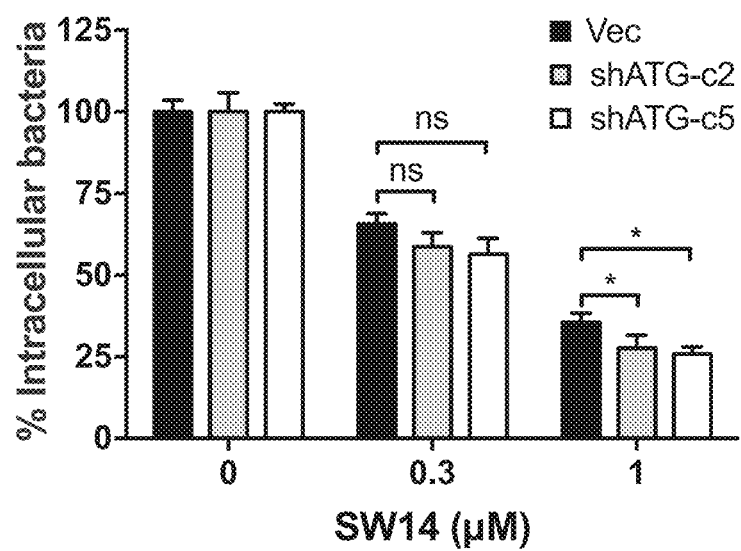
FIG. 9. Intracellular bacterial survival in SW14-treated RAW264.7 cells with shRNA-mediated knockdown of Atg7 expression. RAW264.7 cells were transfected with the empty vector (Vec) and infected with S. typhimurium followed by treatment with 0, 0.3, and 1 μM of SW14 and 20 mg/mL gentamicin for 24 hours. The numbers of surviving intracellular bacteria are determined by HCA and the results are expressed as a percentage of the control group. Intracellular bacterial survival in SW14-treated RAW264.7 cells with shRNA-mediated knockdown of Atg7 expression. Data shown are the means; error bars represent the SD (n=3). ns: non-significant, P>0.05; *P<0.05 for the differences between the drug-treated groups and their respective control groups.

Similar to the 3-MA-mediated blockade of the autophagy pathway, knockdown of Atg7 in RAW264.7 cells also rendered intracellular *Salmonella* more susceptible to the suppressive effects of SW14 according to FIG. 9. It indicates that autophagy did not contribute to the SW14-mediated suppression of intracellular *Salmonella*.

SW14 and Bacterial Oxidative Stress

Figure 10:
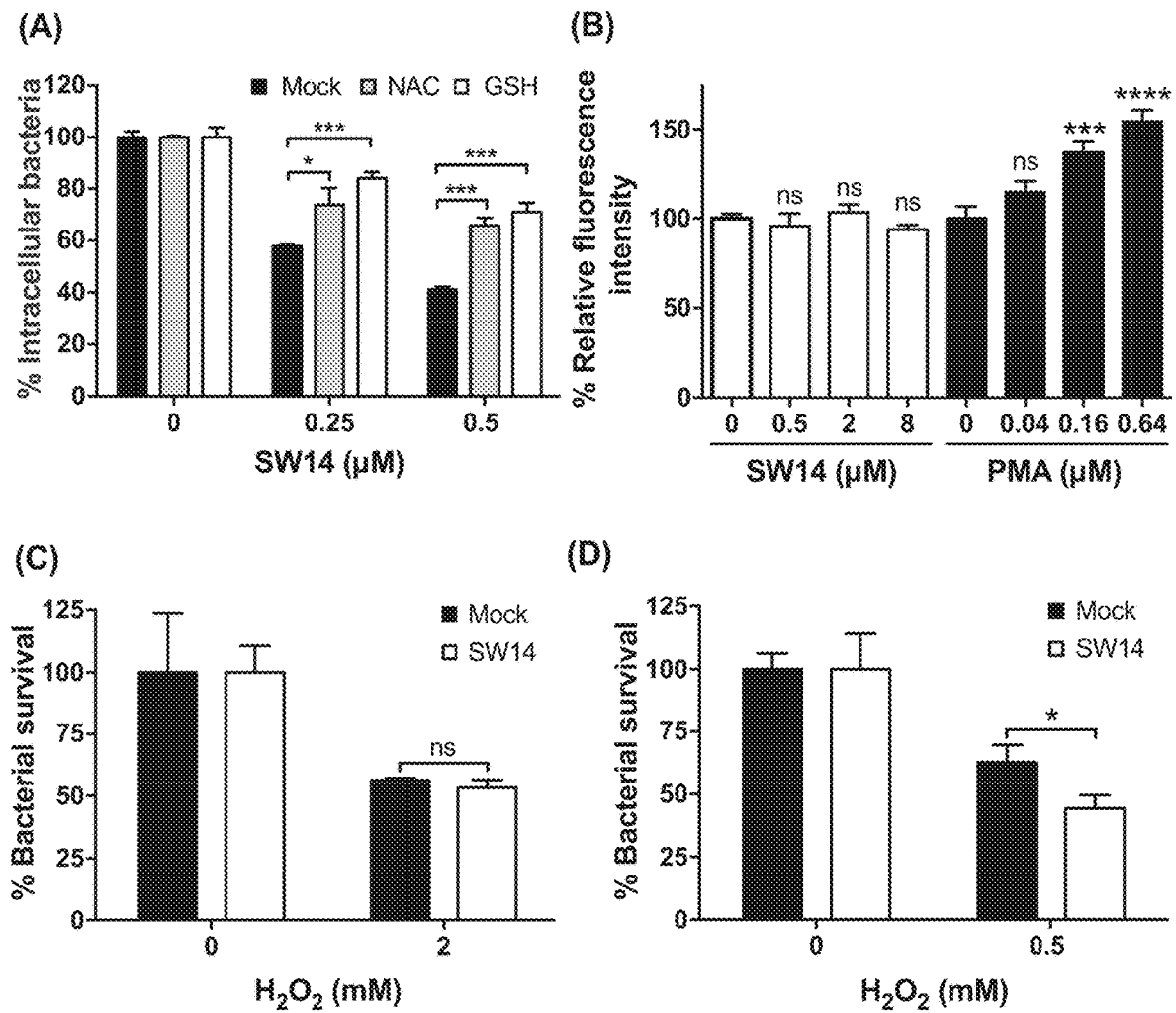
FIG. 10. SW14 sensitizing outer membrane-compromised S. typhimurium to oxidative stress. (A) ROS scavengers reversed the suppressive effects of SW14 on intracellular S. typhimurium. The viabilities of intracellular Salmonella in RAW264.7 cells treated with SW14 with/without the ROS scavengers N-acetyl-cysteine (NAC; 10 mM) or glutathione (GSH; 10 mM) are assessed using HCA. The data are presented as the mean±SD (n=3 per group). * P<0.05; * P<0.001. (B) SW14 does not induce ROS production in macrophages. Salmonella-infected RAW264.7 cells are loaded with 25 μM $H_2DCFDA$ for 45 min followed by treatment with SW14 or PMA at various concentrations. The data are expressed as a percentage relative to the untreated control and are presented as the mean±SD (n=3 per group). ns: non-significant, P>0.05; * P<0.001; ****P<0.0001. S. Typhimurium ATCC 14028 is treated with $H_2O_2$ alone or in combination with SW14 (0.5 μM) in (C) LB or (D) LPM for 1 hour followed by evaluation by the CFU assay to determine bacterial viability. The data are expressed as a percentage relative to the number of bacteria in $H_2O_2$-free medium and are presented as the mean±SD (n=3 per group). ns: non-significant, P>0.05; * P<0.05.

Oxidative stress is another innate defense system in host cells that controls intracellular *Salmonella* infection. In FIG. 10(A), the suppressive effects of SW14 against *S. Typhimu-* rium within macrophages are reversed in the presence of two ROS scavengers, N-acetyl cysteine (NAC) and glutathione (GSH).

To establish whether SW14's anti-intracellular *Salmonella* activity is mediated by ROS induction, loaded *Salmonella*-infected RAW 264.7 cells with the ROS indicator H$_2$DCFDA and treated cells with SW14 or PMA, a known ROS inducer, for 1 hour. As shown in FIG. 10(B), PMA significantly elevated ROS levels in infected macrophages, as demonstrated by the increase in the fluorescence signal of H$_2$DCFDA. In contrast, we did not observe any significant change in the H$_2$DCFDA signal in SW14-treated cells at concentrations up to 8 µM, which is 16 times greater than its EC$_{50}$ against intracellular *Salmonella*.

Next, the effects of SW14 on bacterial resistance to ROS are investigated. According to FIG. 10(C) and (D), the susceptibility of *S. typhimurium* to H$_2$O$_2$ is significantly increasing after SW14 treatment at its EC$_{50}$ concentration (0.5 µM) in LPM medium but not in LB broth. Thus, these results indicate that SW14 can suppress the resistance of *Salmonella* to oxidative stress under conditions that compromise the outer membrane.

In view of the above, the present invention designs the antibacterial chemical compound, its manufacturing method and its use thereof, thereby providing an antibacterial agents being useful for treating a disease or condition characterized by infectious disease, such as gastroenteritis and invasive non-typhoidal Salmonellosis, and also providing a new therapeutic option for patients infected by the bacteria with the resistance to antibiotics.

The above is the detailed description of the present invention. However, the above is merely the preferred embodiment of the present invention and cannot be the limitation to the implement scope of the invention, which means the variation and modification according to the present invention may still fall into the scope of the present invention.

What is claimed is:

1. A compound (I) having following structure:

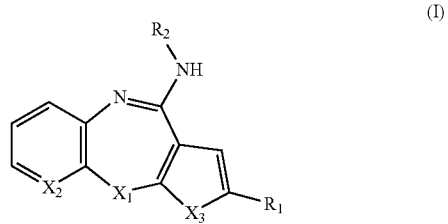

(I)

or a pharmaceutically acceptable salt thereof,
wherein
X$_1$ is O;
X$_2$ is CH;
X$_3$ is CHCH;
R$_1$ is H, CH$_3$ or Cl; and
R$_2$ is

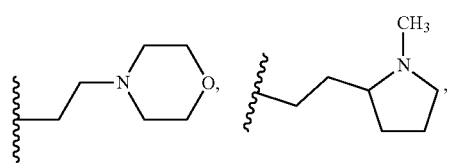

-continued

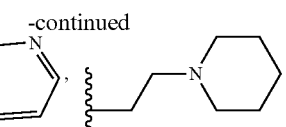

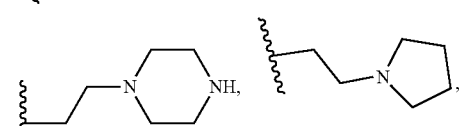

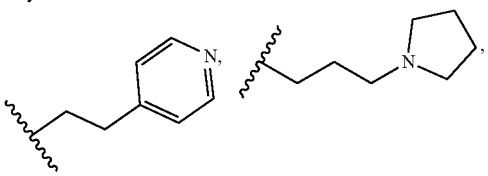

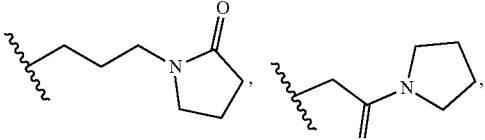

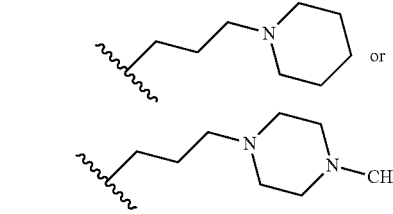

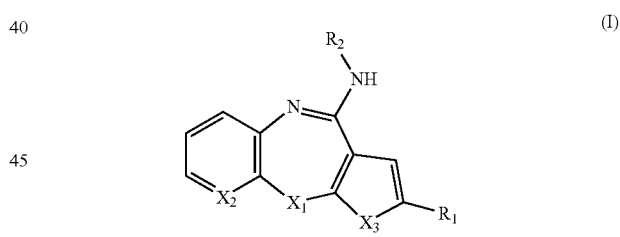

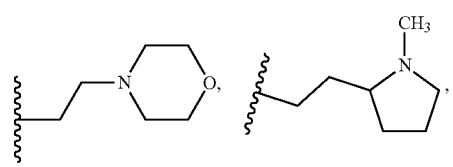

2. A pharmaceutical composition comprising: an effective amount of a compound (I) having following structure:

(I)

or a pharmaceutically acceptable salt thereof,
wherein
X$_1$ is O;
X$_2$ is CH;
X$_3$ is CHCH;
R$_1$ is H, CH$_3$ or Cl; and
R$_2$ is:

-continued

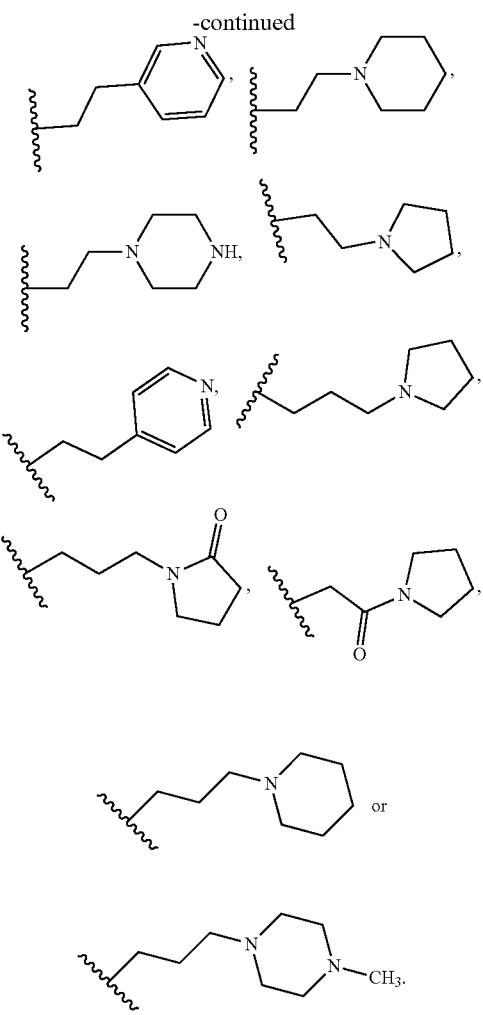

3. The pharmaceutical composition of claim 2, wherein the compound is:

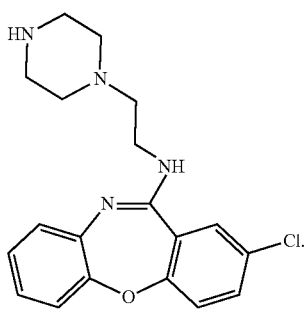 [SMILES: Clc1ccc2c(c1)C(NCCN1CCNCC1)=Nc1ccccc1O2]

4. The pharmaceutical composition of claim 2, further comprising a pharmaceutically acceptable excipient.

5. The pharmaceutical composition of claim 2, further comprising an antibiotic.

6. The pharmaceutical composition of claim 5, which targets a bacteria's resistance to host oxidative-stress defense.

7. The pharmaceutical composition of claim 6, wherein the bacteria is multidrug-resistant strain.

8. The pharmaceutical composition of claim 7, wherein the bacteria is selected from the group consisting of: *Staphylococcus aureus, Staphylococcus haemolyticus, Staphylococcus hominis, Staphylococcus intermedius, Staphylococcus saprophyticus, Staphylococcus lugdunensis, Erysipelothrix rhusiopathiae, Enterococcus faecalis, Enterococcus faecium*, VR-*E. faecium, Bacillus cereus, Bacillus subtilis, Corynebacterium diphtherias, Listeria monocytogenes, Streptococcus pyogenes, Clostridium difficile, Escherichia coli, Salmonella Typhimurium, Acinetobacter baumannii*, and *Mycobacterium tuberculosis*.

9. A method of synthesizing the compound (I) of claim 1, comprising:

(1) reacting a compound (VI) of the following structure

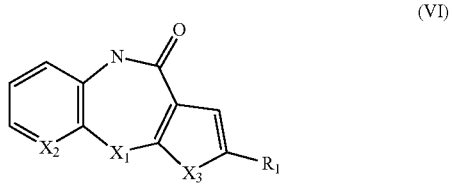

(VI)

with $POCl_3$ and $R_2NH_2$ to obtain the compound (I); or (2) reacting a compound (XVI) of the following structure

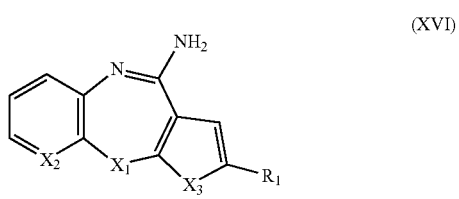

(XVI)

with $R_2NH_2$ to obtain the compound (I);

wherein $X_1$, $X_2$, $X_3$, $R_1$ and $R_2$ are the same as defined in claim 1.

10. The method of claim 9, wherein $X_1$ of the compound (VI) is O and the compound (VI) is obtained by:

(a) under the present of $K_2CO_3$, reacting a compound (II) of following structure

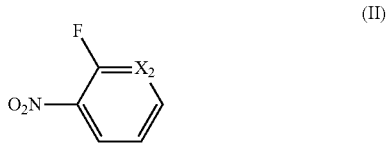

(II)

with a compound (III) of following structure

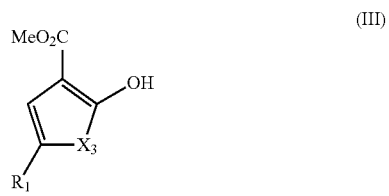

(III)

to obtain a compound (IV) of following structure;

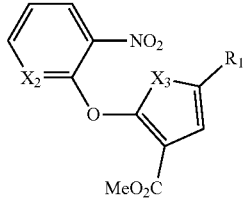
(IV)

(b) reacting the compound (IV) with SnCl$_2$ to obtain a compound (V) of following structure;

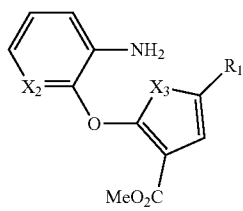
(V)

(c) reacting the compound (V) with H$_2$SO$_4$ to obtain the compound (VI);
wherein
X$_2$ is CH;
X$_3$ is —CHCH—;
R$_1$ is H, CH$_3$ or Cl; and
R$_2$ is

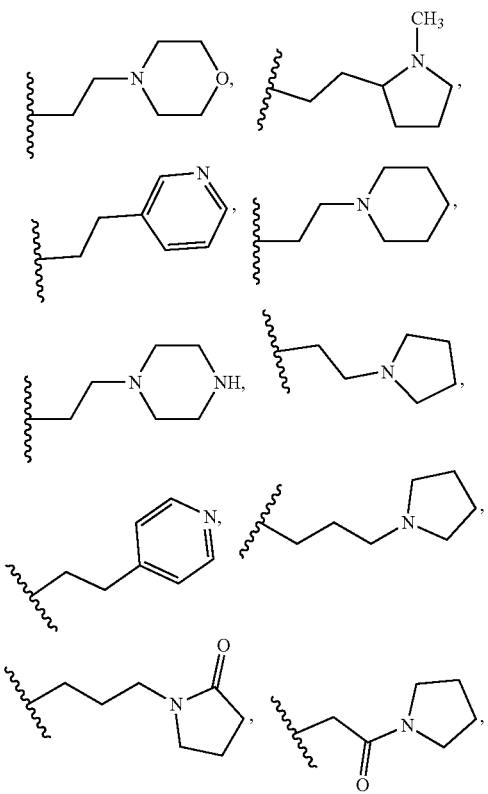

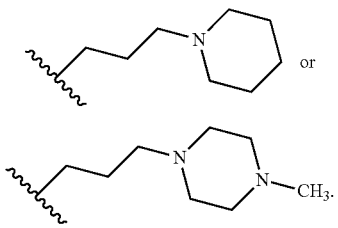

11. The method of claim 9, wherein X$_1$ of the compound (VI) is NH and the compound (VI) is obtained by:

(a) under the present of SOCl$_2$, reacting a compound (VII) of following structure

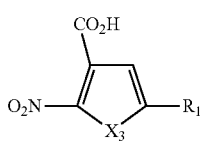
(VII)

with a compound (VIII) of following structure

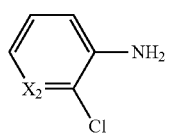
(VIII)

to obtain a compound (IX) of following structure;

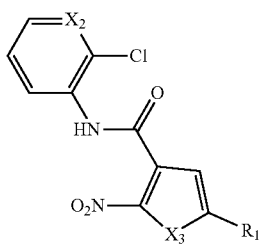
(IX)

(b) reacting the compound (IX) with SnCl$_2$ to obtain a compound (X) of following structure;

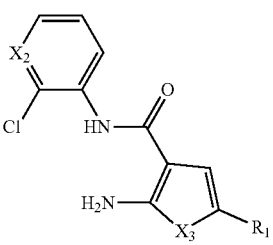
(X)

(c) reacting the compound (X) with DEGMME to obtain the compound (VI);

wherein $X_2$ is CH;

$X_3$ is —CHCH;

$R_1$ is H, $CH_3$ or Cl; and $R_2$ is

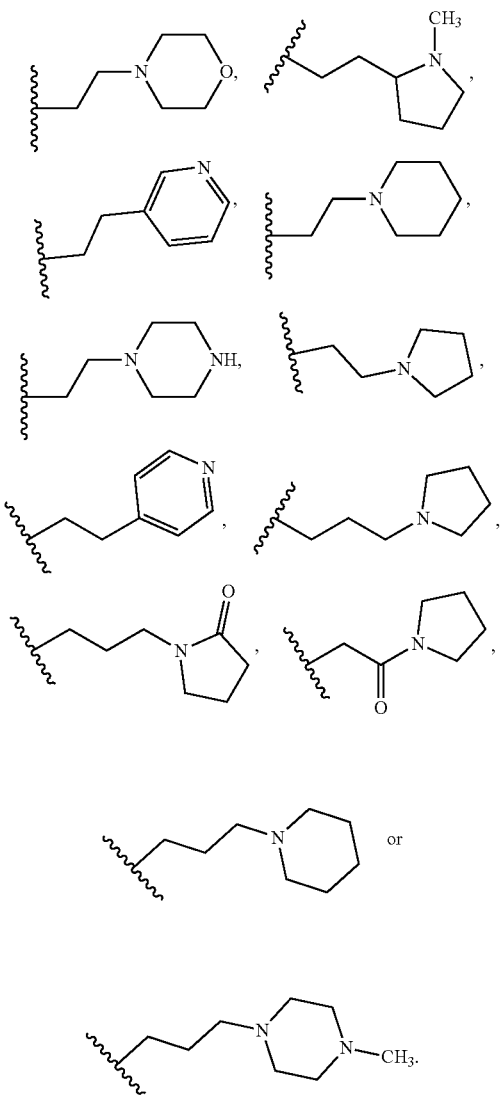

12. The method of claim 10, wherein $X_1$ is NH and the compound (VI) is obtained by:

(a) reacting a compound (XI) of following structure

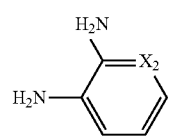

(XI)

with a compound (XII) of following structure with Cu and $K_2CO_3$

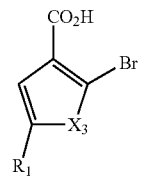

(XII)

to obtain a compound (XIII) of following structure;

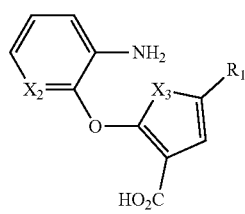

(XIII)

(b) reacting the compound (XIII) with $H_2SO_4$ to obtain the compound (VI);

wherein $X_2$ is CH;

$X_3$ is —CHCH;

$R_1$ is H, $CH_3$ or Cl; and $R_2$ is

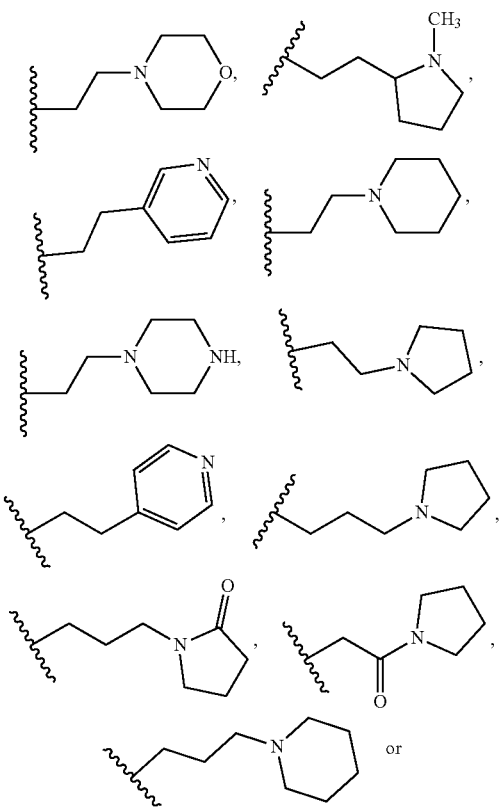

-continued
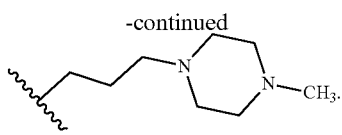
13. The method of claim 10, wherein $X_1$ is NH and the compound (XVI) is obtained by:
(a) reacting a compound (II) of following structure
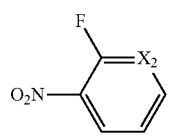
(II)
with a compound (XIV) of following structure
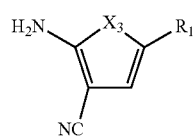
(XIV)
to obtain a compound (XV) of following structure;
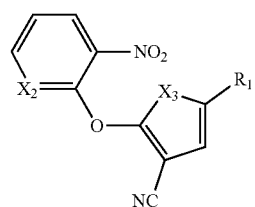
(XV)
(b) reacting the compound (XV) with $SnCl_2$ and HCl to obtain the compound (XVI);
wherein
$X_2$ is CH;
$X_3$ is —CHCH;
$R_1$ is H, $CH_3$ or Cl; and
$R_2$ is
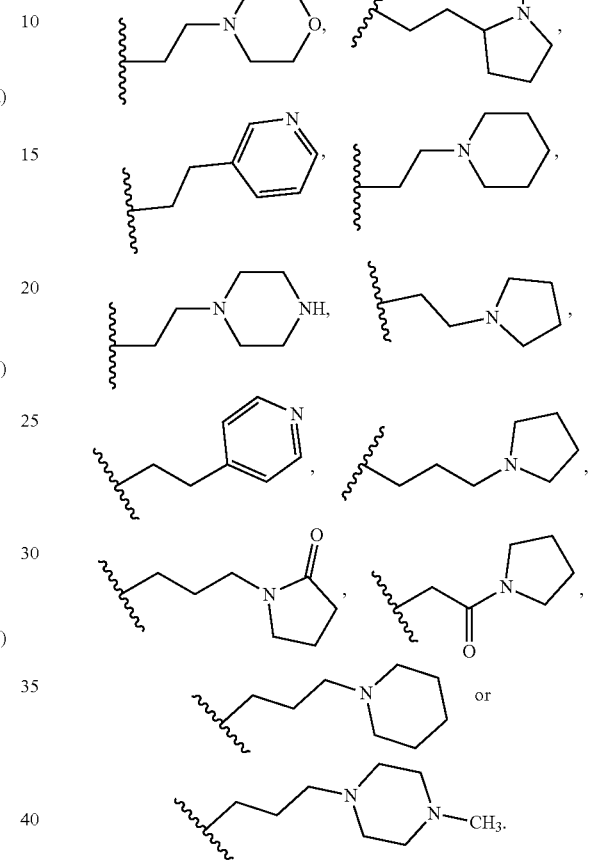
* * * * *